United States Patent [19]

Montzka et al.

[11] 3,956,336

[45] May 11, 1976

[54] 9-ALKOXY-5-METHYL-6,7-BENZOMORPHANS

[75] Inventors: Thomas Alfred Montzka, Manlius; John Daniel Matiskella, Liverpool, both of N.Y.

[73] Assignee: Bristol-Myers Company, New York, N.Y.

[22] Filed: Mar. 26, 1975

[21] Appl. No.: 562,077

Related U.S. Application Data

[63] Continuation-in-part of Ser. No. 462,007, April 18, 1974, abandoned.

[52] U.S. Cl. .................... 260/293.54; 260/247.2 B; 260/247.5 GP; 260/DIG. 13; 424/248; 424/267
[51] Int. Cl.² ........................................ C07D 39/00
[58] Field of Search ............... 260/293.54, DIG. 13; 260/247.2 B, 247.5 GP

[56] References Cited
UNITED STATES PATENTS 3,639,407  2/1972  Clarke et al. ................ 260/293.54
3,891,657  6/1975  Monkovic et al. ............ 260/293.54

OTHER PUBLICATIONS

May, et al., J. Org. Chem. 25: 1386 (1960).
May, et al., J. Org. Chem. 26: 188 (1961).
May, et al., J. Org. Chem. 26, 1621 (1961).
May, et al., J. Org. Chem. 26: 1954 (1961).
May, et al., J. Org. Chem. 26: 4536 (1961).
May, et al., J. Med. Chem. 8: 235 (1965).

*Primary Examiner*—Henry R. Jiles
*Assistant Examiner*—C. M. S. Jaisle
*Attorney, Agent, or Firm*—Robert E. Havranek

[57] ABSTRACT

N-Substituted-9-alkoxy-5-methyl-6,7-benzomorphans have been found to possess potent narcotic agonist and/or antagonist activity. In particular, the compound 2-cyclopropylmethyl-2'-hydroxy-9α-methoxy-5-methyl-6,7-benzomorphan has been found to possess potent narcotic agonist and antagonist activity. These compounds are prepared by total synthesis and are not derived from opium alkaloids.

34 Claims, No Drawings

9-ALKOXY-5-METHYL-6,7-BENZOMORPHANS

BACKGROUND OF THE INVENTION

This application is a continuation-in-part of a copending application Ser. No. 462,007, filed Apr. 18, 1974 now abandoned.

FIELD OF THE INVENTION

This invention embodies new and novel compounds useful as analgesics and/or narcotic antagonists and a new and novel total synthesis for their preparation.

DESCRIPTION OF THE PRIOR ART

A. Everette May and Hiroshi Kugita, J. Org. Chem. 188 (1961) describe compounds having the formula

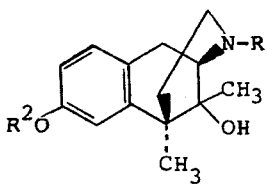

in which $R^2$ is H or methyl and R is methyl or phenethyl as being moderate to weak analgetics.

B. Everette May, James Murphy and J. Harrison Ager, J. Org. Chem. 25, 1386 (1960) report compounds having the formula

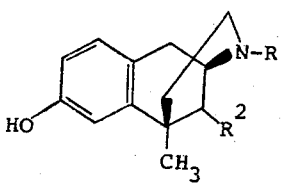

in which R is methyl or phenethyl and $R^2$ is H or methyl as being potent analgetics.

C. Everette May, Hiroshi Kugita and J. Harrison Ager, J. Org. Chem. 26, 1621 (1961) report compounds havig the formula

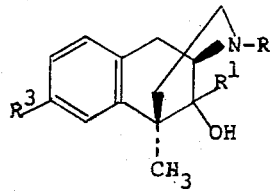

in which R is methyl or phenethyl, $R^1$ is methyl or H, $R^3$ is H, OH or methoxy as producing varying degrees of analgesia.

D. Everette May, Colin Chignell and J. Harrison Ager, J. Med. Chem. 8, 235 (1965) report compounds having the formula

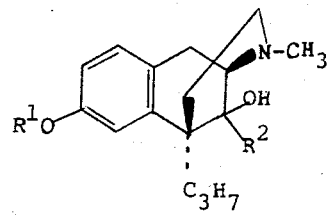

in which $R^1$ is H or methyl and $R^2$ is methyl as possessing analgetic activity.

E. Everette May and Hiroshi Kugita, J. Org. Chem., 26, 1954 (1961) report the compound having the formula

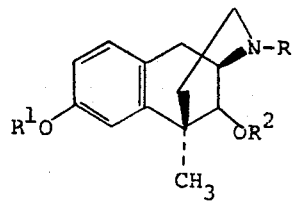

in which R is methyl or phenethyl, $R^1$ is H or methyl and $R^2$ is H or acetyl as having analgetic activity.

G. Everette May and Seiichi Sato, J. Org. Chem. 26, 4536 (1961) report compounds having the formula

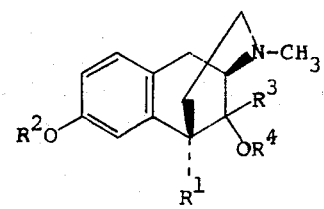

in which $R^2$ is H or methyl, $R^1$ is methyl or ethyl, $R^3$ is methyl or ethyl and $R^4$ is H or acetyl as possessing analgetic activity.

H. N. B. Eddy and E. L. May published a review of 6,7-benzomorphans in Synthetic Analgetics, Pergamon Press (1966).

SUMMARY OF THE INVENTION

Compounds having the formula

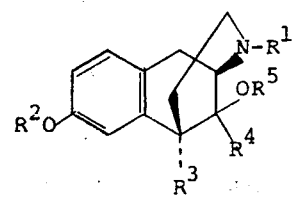

L wherein $R^1$ is selected from the group comprising $-CH_2-C \equiv CH$, $-CH_2-CH=CH_2$,

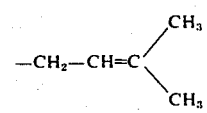

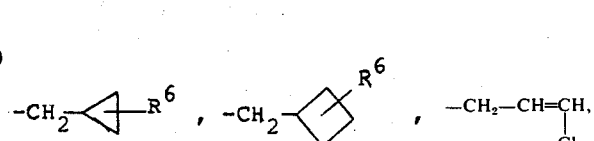

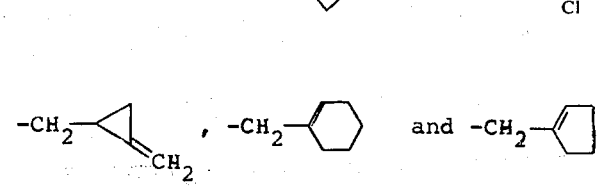
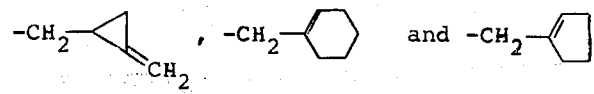

in which $R^6$ is H or $CH_3$, $R^2$ is selected from the group comprising H, (lower)alkyl, (lower)alkanoyl,

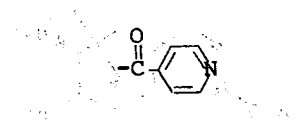

and

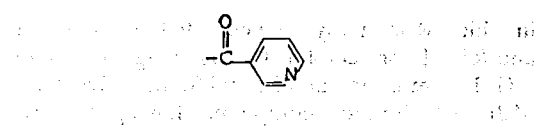

$R^5$ is (lower)alkyl, propargyl, or allyl, $R^3$ is (lower)alkyl or (lower)alkenyl and $R^4$ is H or (lower)alkyl; or a pharmaceutically acceptable acid addition salt thereof are analgetic agents, narcotic antagonists or intermediates in the preparation of such agents.

DISCLOSURE OF THE INVENTION

This invention relates to the total synthesis of new and novel N-substituted-9-alkoxy-5-alkyl- and alkenyl-6,7-benzomorphans having the formula

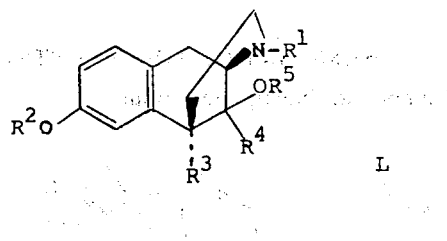 L wherein $R^1$ is selected from the group comprising H, $-CH_2-C \equiv CH$, $-CH_2-CH=CH_2$,

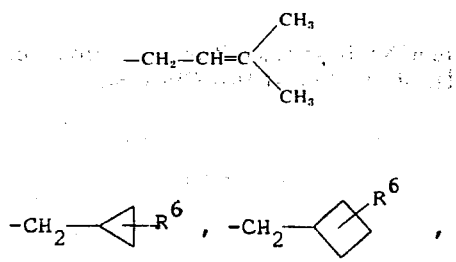

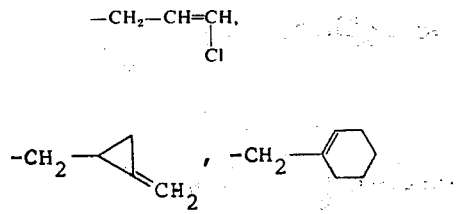

and

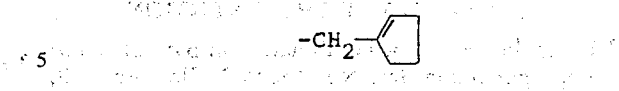

in which $R^6$ is H or $CH_3$, $R^2$ is selected from the group comprising H, (lower)alkyl, (lower)alkanoyl,

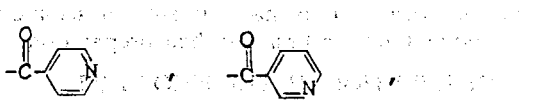

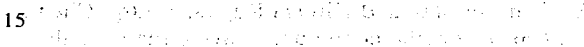

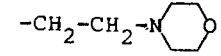

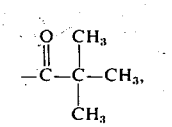

$R^5$ is (lower)alkyl, allyl or propargyl, $R^4$ is H or (lower)alkyl and $R^3$ is (lower)alkyl or (lower)alkenyl; or a pharmaceutically acceptable acid addition salt thereof.

Drug abuse by thrill-seeking youth or by people looking for an escape from the realities of every day life has become more and more common place in our present society. One class of widely abused drugs are the narcotic analgetics such as codeine, morphine, meperidine, etc. It is because of the high addictive potential of these agents that much time and money are being expended by the pharmaceutical industry and by governments to try and discover and develop new non-addicting analgetics and/or narcotic antagonists.

It was therefore an object of the present invention to find new and novel compounds that have these characteristics.

It was further an object of the present invention to develop a method of synthesis that would not be dependent upon opium alkaloids as starting materials and yet would be commercially feasible.

The objectives of the present invention have been achieved by the provision of compounds of formula L and by their total synthesis from the readily available starting material 7-methoxy-3,4-dihydro-2[1H]-naphthalenone (I).

The compounds of the instant invention have the basic benzomorphan nucleus which is numbered and represented by the following plane formula

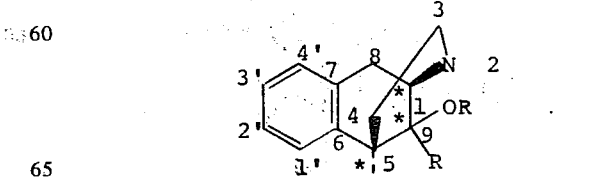

Although there are three asymmetric carbons (asterisks) in the benzomorphan molecule, only two racemic forms are possible, because the iminoethano system, attached to position 1 and 5, is geometrically contained to a cis-(1,3-diaxial)-fusion. These racemates can therefore differ only in the configuration of carbon 9. The only variable will be the cis and trans relationship of the 9-alkoxy compound to the iminoethano system. When in the compounds of the present invention the 9-alkoxy is trans to the iminoethano system, we have the 9α-alkoxybenzomorphans. When the 9-alkoxy is cis to the iminoethano system, we have the 9β-alkoxybenzomorphans.

The use of a graphic representation of a benzomorphan is meant to include the dl racemic mixture and the resolved d and l isomers thereof.

The compounds of the present invention, eg., the 9α-alkoxybenzomorphans, can exist as two optical isomers, the levorotatory and dextrorotatory isomers. The optical isomers can be graphically illustrated as:

9α-Methoxybenzomorphan:

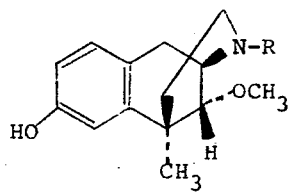

and

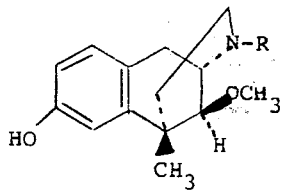

The present invention embodies all of the isomers including the optical isomes in their resolved form.

The optical isomers can be separated and isolated by fractional crystallization of the diastereoisomeric salts formed, for instance, with d- or l- tartaric acid or D-(+)-α-bromocamphor sulfonic acid. The levorotatory isomers of the compounds of the present invention are the most preferred embodiments. Other acids commonly used for resolution can also be employed.

For the purpose of this disclosure, the term "(lower)alkyl" is defined as an alkyl radical containing 1 to 6 carbon atoms. "(Lower)alkenyl" is defined as a hydrocarbon radical of 2 to 6 carbons containing one double bond. The term "(lower)alkanoyl" is an acyl radical of 2 to 6 carbon atoms, e.g., acetyl, propionyl, isobutyryl, etc. The term "pharmaceutically acceptable acid addition salt" is defined to include all those inorganic and organic acid salts of the compounds of the instant invention, which acids are commonly used to produce essentially nontoxic salts of medicinal agents containing amine functions. Illustrative examples would be those salts formed by mixing the compounds of formula L with hydrochloric, sulfuric, nitric, phosphoric, phosphorous, hydrobromic, maleic, malic, ascorbic, citric or tartaric, pamoic, lauric, stearic, palmitic, oleic, myristic, lauryl sulfonic, napthalenesulfonic, linoleic or linolenic acid, fumaric, and the like.

The compounds of the instant invention are prepared by a total synthesis comprising multiple steps. Surprisingly, the synthesis is efficient and appears commercially feasible. A representation of the process is outlined in Charts I and II.

CHART I

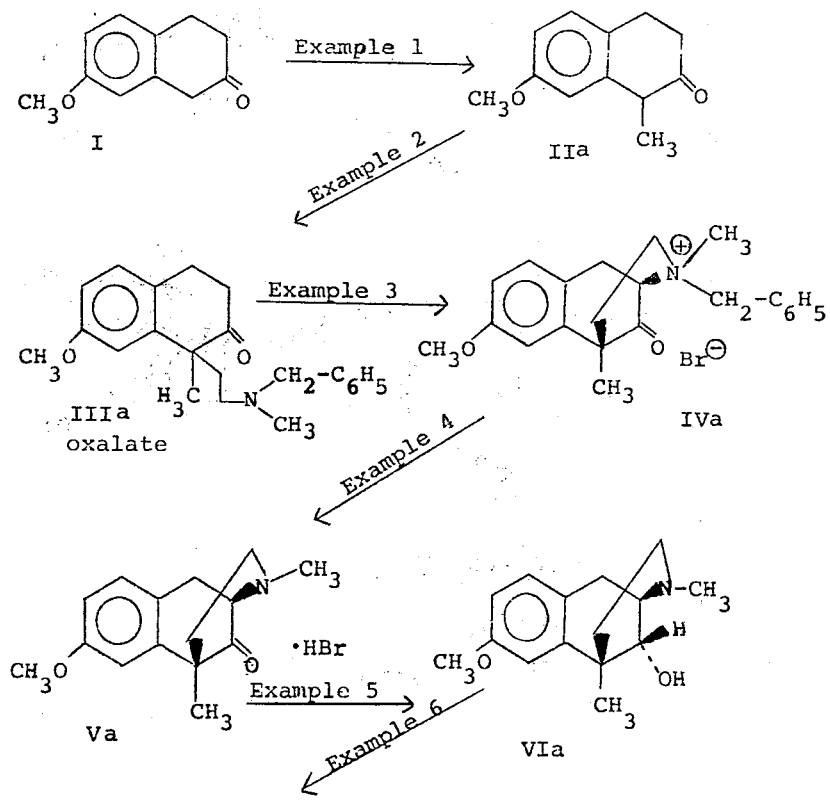

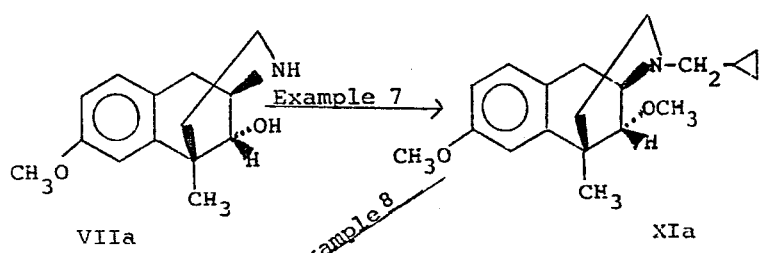
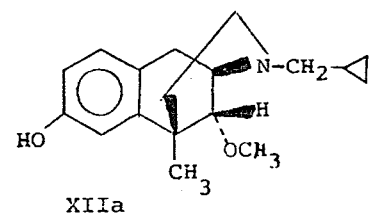
CHART II
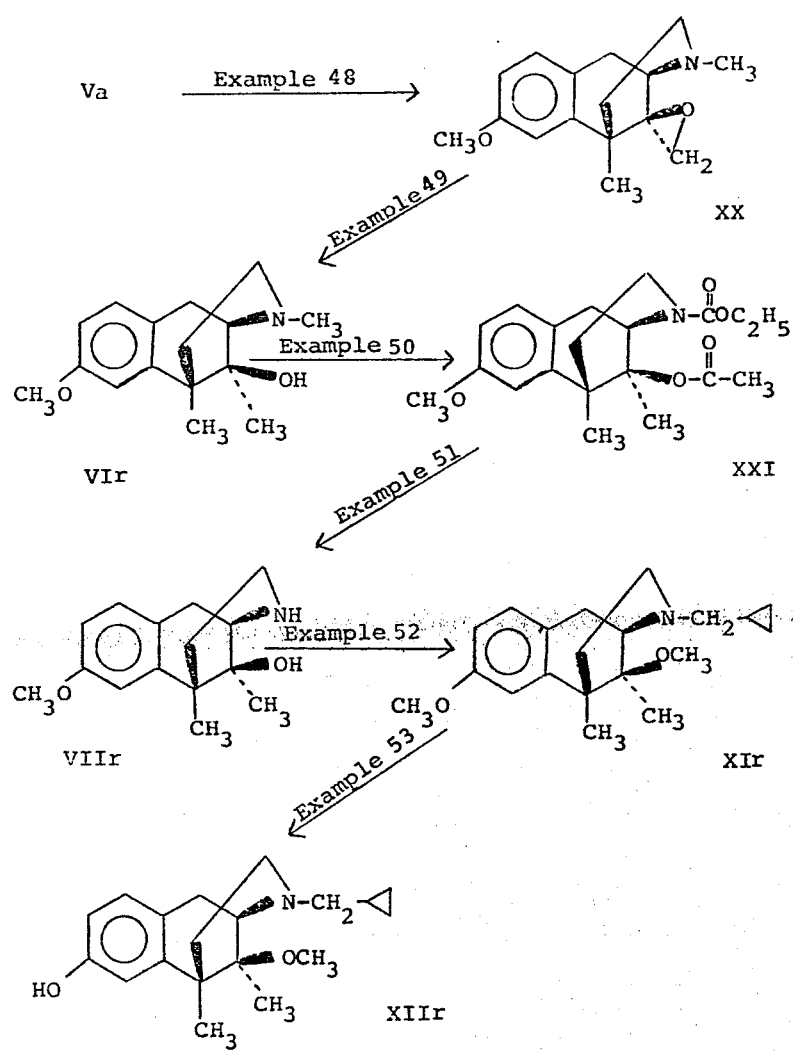

Compounds having the formula

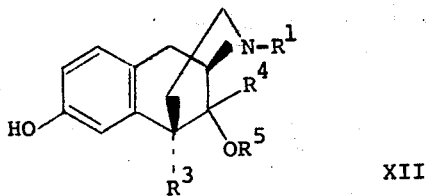

wherein R¹ is selected from the group consisting of H, —CH₂—C≡CH, —CH₂—CH=CH₂,

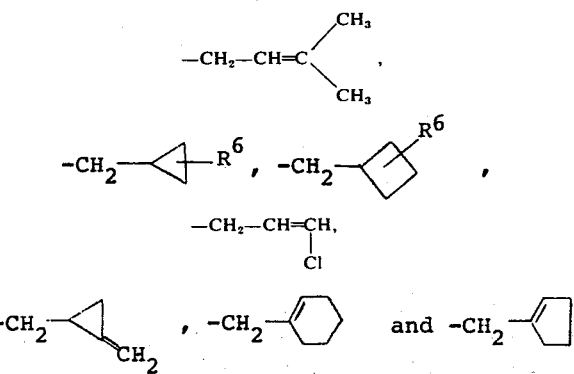

in which $R^6$ is H or $CH_3$; $R^5$ is selected from the group consisting of (lower)alkyl, allyl and propargyl, $R^4$ is H or (lower)alkyl and $R^3$ is (lower)alkyl or (lower)alkenyl; or a pharmaceutically acceptable acid addition salt thereof are valuable as narcotic agonist/antagonist agents or as intermediates in the preparation thereof.

All of the compounds of the preferred embodiments herein are novel and valuable for their properties as analgesic and/or narcotic antagonist agents, or as intermediates in the preparation of compounds having these biological activities.

In particular, the compounds having the formula XII are those which possess the most desirable properties; i.e., analgesic and/or narcotic antagonist properties. Some of these compounds also possess antitussive activity, a property generally inherent with analgetic activity.

The most potent and desirable compounds of the invention are those of formula XII in which $R^4$ is $9\beta$-hydrogen and $OR^5$ is $9\alpha$-alkoxy. This is a surprising finding in view of the fact that in the corresponding series of compounds in which $OR^5$ is OH, the most potent and desirable compounds generally have a $9\beta$-OH and a $9\alpha$-hydrogen or (lower)alkyl.

It is well known in the narcotic analgesic prior art that it is possible for some compounds to possess both agonist and antagonist properties. An agonist is a compound that imitates a narcotic analgesic and possesses analgetic qualities. An antagonist is a compound that counteracts the analgetic and euphoric properties of a narcotic analgetic. It is possible for a compound to have both properties. A good example of such a compound is cyclazocine.

Discovering compounds that have the proper ratio of agonist/antagonist activity is crucial to commercial success. Compounds having too much antagonist activity tend to produce unwanted psychotomimetic effects (hallucinations) thereby rendering the compounds undesirable for clinical use.

In vivo testing was conducted on various compounds of the instant invention in the form of their respective soluble salts to determine their agonist and/or antagonist properties. Table I represents the results of the experiments. The figures reported are the number of milligrams/kilogram of body weight of compound that produced an agonist or antagonist effect in 50% of the mice and rats so tested ($ED_{50}$). All data is obtained by subcutaneous administration.

TABLE I

| | Agonist Activity Phenylquinone[1] Writhing | | $ED_{50}$ (mg./kg.)[6] Antagonist Activity | | |
|---|---|---|---|---|---|
| | | | Oxymorphone[2] Straub Tail | Oxymorphone[3] Narcosis | Morphine Antagonism[4] Rat Tail Flick |
| Test Compounds | Mouse | Rat | | | |
| dl-XIIa | 0.087 | 0.034 | 0.24 | 0.04 | 0.06 |
| l-XIIa | 0.053 | 0.021 | 0.10 | 0.017 | 0.019 |
| dl-XIIb | 1.25 | N.D. | 0.16 | ~0.017 | 0.011 |
| dl-XIIc | 2.18 | N.D. | 1.25 | N.D. | N.D. |
| dl-XIIe | 5.30 | N.D. | ~0.63 | N.D. | N.D. |
| dl-XIId | 0.33 | N.D. | 0.32 | N.D. | 0.029 |
| dl-XIIr | 1.8 | N.D. | 3.5 | N.D. | N.D. |
| dl-XIIv | 0.19 | N.D. | 7.5 | N.D. | N.D. |
| Pentazocine | 4.9 | N.D. | 12.0 | 10.1 | 12.2 |
| Nalorphine | 0.77 | N.D. | 1.14 | 0.58 | 0.38 |
| Levallorphan | 26.3 (poor dose response) | N.D. | 0.29 | 0.32 | 0.086 |
| Cyclazocine | 0.047 | N.D. | 0.81 | 0.12 | 0.040 |
| Naloxone | 40 | N.D. | 0.17 | 0.02 | 0.010 |
| dl-XIIm | 0.026 | N.D. | N.D. | N.D. | 0.046 |
| dl-XIIn | 0.20 | N.D. | N.D. | N.D. | 0.033 |
| dl-XIIt | ~20 | N.D. | ~7 | N.D. | 0.18 |

[1]A 50 percent reduction in number of phenylquinone induced writhings (Siegmund, E. A. et al., Proc. Soc. Biol. & Med. 95, 729; 1957).
[2]Antagonism of Straub Tail induced by oxymorphone (2 mg./kg. sc.) in 50 percent of mice.
[3]Antagonism of righting reflex loss induced by oxymorphone (1.5 mg./kg. sc.) in 50 percent of rats.
[4]A 50 percent cent reduction of analgesic effect induced by morphine (15 mg./kg. sc.) as measured by the rat tail flick procedure (Harris, L. S. and Pierson, A. K., J. Pharmacol. & Expt. Therap., 143, 141; 1964).
[5]N.D. - Not done.
[6]All weights reported are corrected to read in terms of the free base.

It is apparent from the testing that the compounds have potent agonist and antagonist activity. The normal parenteral dosage range of the compounds of the present invention in adult humans is about 0.25 to 10 mg. three to four times a day. Orally the dose is in the range of about 1 to 50 mg. three or four times a day.

It has been reported in the literature that the compound haloperidol, 4[4-(p-chlorophenyl)-4-hydroxypiperidino]-4'-fluorobutyrophenone (Merck Index, 8th Edition, p. 515) has found some experimental use in the alleviation of narcotic addiction withdrawal symptoms. It is therefore a preferred embodiment of the present invention to combine haloperidol with the narcotic antagonists of the instant invention to produce a product not only preventing narcotic abuse, but at the same time providing supportive therapy in the absence of opiates.

Haloperidol is commonly administered orally in a dose of 0.5 to 5.0 mg. two or three times daily depending upon the severity of the illness. A dose of haloperidol in this range would be administered contemporaneously with an effective dose of the narcotic antagonist to produce the desired result.

Other combinations would include the narcotic antagonists in combination with anti-anxiety agents such as chlorodiazepoxide and diazepam, or phenothiazines like chlorpromazine, promazine or methotrimeptrazine.

The compounds designated XII herein are readily transformed into derivatives designated by the formula L. These esters and ethers of XII may in some cases have special advantage due to increased solubility, decreased solubility, ease of crystallization, lack of objectionable taste, etc., but these are all subsidiary to the main physiological action of the free phenol which is independent of the character of the radical used in the preparation of the ester or ether.

A preferred embodiment is the compound having the formula

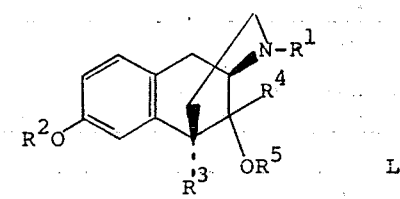

L wherein $R^1$ is selected from the group consisting of H, —$CH_2$—C ≡ CH, —$CH_2$—CH=$CH_2$,

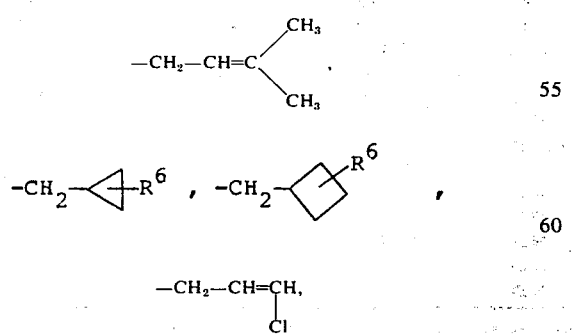

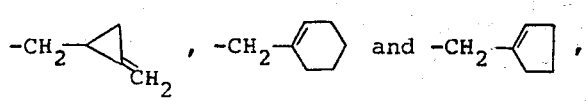

in which $R^6$ is H or $CH_3$; $R^2$ is selected from the group consisting of H, (lower)alkyl, (lower)alkanoyl,

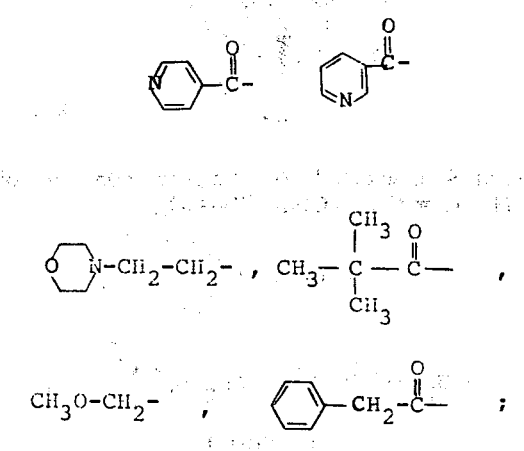

$R^5$ is selected from the group consisting of (lower)alkyl, allyl and propargyl, $R^4$ is H or (lower)alkyl and $R^3$ is (lower)alkyl or (lower)alkenyl; or a pharmaceutically acceptable acid addition salt thereof.

A more preferred embodiment is a compound having the formula

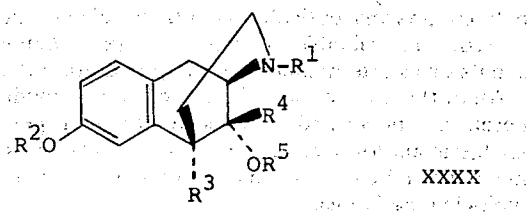

XXXX wherein $R^1$ is selected from the group consisting of H, —$CH_2$—C ≡ CH, —$CH_2$—CH=$CH_2$,

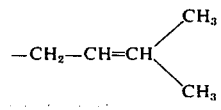

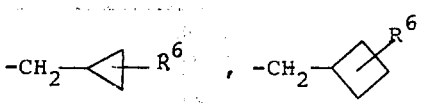

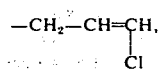

in which $R^6$ is H or $CH_3$; $R^2$ is selected from the group consisting of H, (lower)alkyl, (lower)alkanoyl,

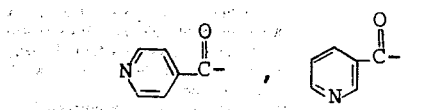

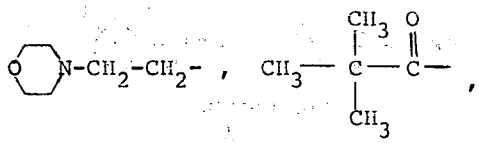, 

CH₃O—CH₂—, 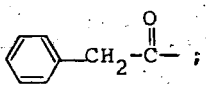

R⁵ is selected from the group consisting of (lower)alkyl, allyl and propargyl, R⁴ is H or (lower)alkyl and R³ is (lower)alkyl or (lower)alkenyl; or a pharmaceutically acceptable acid addition salt thereof.

A more preferred embodiment is the compound of formula XXXX wherein R¹ is —CH₂—C≡CH, —CH₂—CH=CH₂,

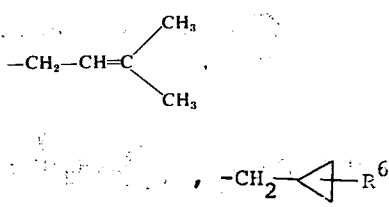

in which R⁶ is H or CH₃, R² is H, CH₃,

or

and R⁵ is CH₃, C₂H₅, propyl, allyl or propargyl, R⁴ is H and R³ is CH₃, ethyl, propyl or allyl; or a pharmaceutically acceptable acid addition salt thereof.

A more preferred embodiment is the compound of formula XXXX wherein R¹ is —CH₂—CH=CH₂,

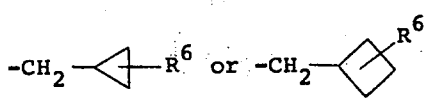

in which R⁶ is H or or CH₃, R² is H,

or

and R⁵ is CH₃, C₂H₅, propyl, allyl or propargyl, R⁴ is H and R³ is CH₃; or a pharmaceutically acceptable acid addition salt thereof.

Another more preferred embodiment is a compound of formula XXXX wherein R¹ is

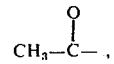

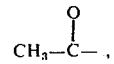

or —CH₂—CH=CH₂, R² is H, CH₃ or

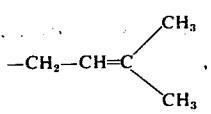

R₅ is methyl, R⁴ is H and R³ is methyl; or a Pharmaceutically acceptable acid addition salt thereof.

Most preferred embodiments are:
A. (±)-2-Cyclopropylmethyl-2′-hydroxy-9α-methoxy-5-methyl-6,7-benzomorphan; or an acid addition salt thereof.
B. (−)-2-Cyclopropylmethyl-2′-hydroxy-9α-methoxy-5-methyl-6,7-benzomorphan; or the hydrochloride, fumarate or tartrate salt thereof.
C. (±)-2-Cyclobutylmethyl-2′-hydroxy-9α-methoxy-5-methyl-6,7-benzomorphan; or an acid addition salt thereof.
D. (−)-2-Cyclobutylmethyl-2′-hydroxy-9α-methoxy-5-methyl-6,7-benzomorphan; or the hydrochloride, fumarate or tartrate salt thereof.
E. (±)-2-Allyl-2′-hydroxy-9α-methoxy-5-methyl-6,7-benzomorphan; or an acid addition salt thereof.
F. (−)-2-Allyl-2′-hydroxy-9α-methoxy-5-methyl-6,7-benzomorphan; or the hydrochloride, fumarate or tartrate salt thereof.
G. (±)-2-Cyclopropylmethyl-9α-ethoxy-2′-hydroxy-5-methyl-6,7-benzomorphan; or a pharmaceutically acceptable acid addition salt thereof.
H. (−)-2-Cyclopropylmethyl-9α-ethoxy-2′-hydroxy-5-methyl-6,7-benzomorphan; or the hydrochloride, fumarate or tartrate salt thereof.
I. (±)-2-Cyclopropylmethyl-2′-hydroxy-9α-methoxy-5-Allyl-6,7-benzomorphan; or an acid addition salt thereof.
J. (−)-2-Cyclopropylmethyl-2′-hydroxy-9α-methoxy-5-Allyl-6,7-benzomorphan; or the hydrochloride, fumarate or tartrate salt thereof.
K. (±)-2-Cyclobutylmethyl-2′-hydroxy-9α-methoxy-5-Allyl-6,7-benzomorphan; or an acid addition salt thereof.
L. (−)-2-Cyclobutylmethyl-2′-hydroxy-9α-methoxy-5-Allyl-6,7-benzomorphan; or the hydrochloride, fumarate or tartrate salt thereof.
M. (±)-2-Cyclopropylmethyl-2′-hydroxy-9α-methoxy-5-propyl-6,7-benzomorphan; or an acid addition salt thereof.
N (−)-2-Cyclopropylmethyl-2′-hydroxy-9α-methoxy-5-propyl-6,7-benzomorphan; or the hydrochloride, fumarate or tartrate salt thereof.
O. (±)-2-Cyclobutylmethyl-2′-hydroxy-9α-methoxy-5-propyl-6,7-benzomorphan; or an acid addition salt thereof.
P. (−)-2-Cyclobutylmethyl-2′-hydroxy-9α-methoxy-5-propyl-6,7-benzomorphan; or the hydrochloride, fumarate or tartrate salt thereof.
Q. (−)-5-Allyl-2-cyclobutylmethyl-2′-hydroxy-9α-methoxy-9β-methyl-6,7-benzomorphan; or the hydrochloride, tartrate or fumarate salt thereof.

R. (−)-2-Cyclobutylmethyl-2′-hydroxy-9α-methoxy-9β-methyl-5-n-propyl-6,7-benzomorphan; or the hydrochloride, tartrate or fumarate salt thereof.

S. (−)-5-Allyl-2-cyclopropylmethyl-2′-hydroxy-9α-methoxy-9β-methyl-6,7-benzomorphan; or the hydrochloride, tartrate or fumarate salt thereof.

T. (−)-2-Cyclopropylmethyl-2′-hydroxy-9α-methoxy-9β-methyl-5-n-propyl-6,7-benzomorphan; or the hydrochloride, tartrate or fumarate salt thereof.

U. The compound having the formula

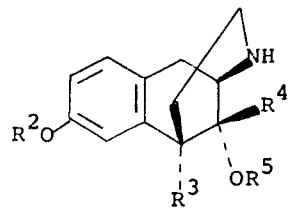

in which $R^2$ is (lower)alkyl, $R^3$ is (lower)alkyl or (lower)alkenyl, $R^4$ is H or (lower)alkyl and $R^5$ is (lower)alkyl, allyl or propargyl; or an acid addition salt thereof.

V. The compound of U supra wherein $R^2$ is methyl, $R^3$ is methyl, ethyl, n-propyl or allyl, $R^4$ is H or methyl and $R^5$ is methyl, ethyl or n-propyl; or an acid addition salt thereof.

W. The compound of U supra wherein $R^2$ is methyl, $R^3$ is methyl, $R^4$ is H and $R^5$ is methyl; or an acid addition salt thereof.

X. The essentially pure levorotatory and dextrorotatory isomers of the compound described in U supra.

Another embodiment is a compound having the formula

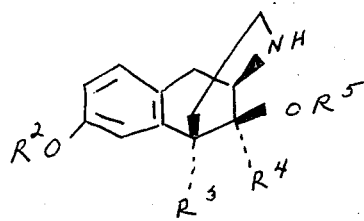

in which $R^2$ is (lower)alkyl, $R^3$ is (lower)alkyl or (lower)alkenyl, $R^4$ is H or (lower)alkyl and $R^5$ is (lower)alkyl, allyl or propargyl; or an acid addition salt thereof.

Another preferred embodiment is a compound having the formula

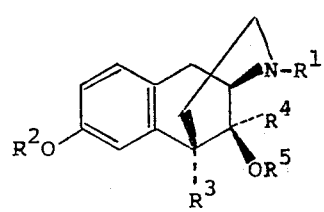 XXXXI wherein $R^1$ is selected from the group consisting of H, $-CH_2-C\equiv CH$, $-CH_2-CH=CH_2$,

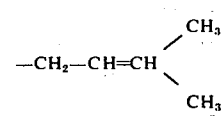

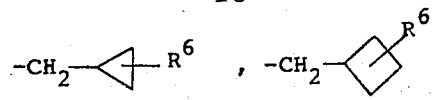

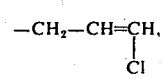

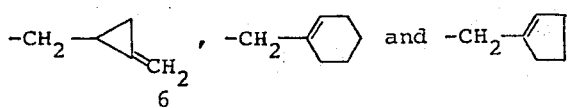

in which $R^6$ is H or $CH_3$; $R^2$ is selected from the group consisting of H, (lower)alkyl, (lower)alkanoyl,

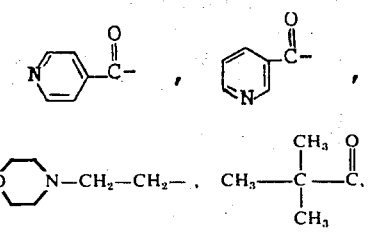

$R^5$ is selected from the group consisting of (lower)alkyl, allyl and propargyl, $R^4$ is H or (lower)alkyl and $R^3$ is (lower)alkyl or (lower)alkenyl; or a pharmaceutically acceptable acid addition salt thereof.

A more preferred embodiment is a compound of formula XXXXI wherein $R^1$ is $-CH_2-C\equiv CH$, $-CH_2-CH=CH_2$,

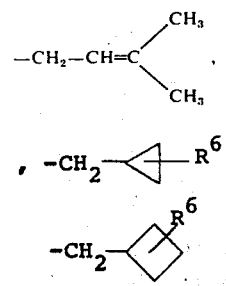

in which $R^6$ is H or $CH_3$, $R^2$ is H,

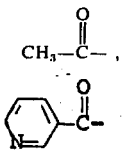

and $R^5$ is $CH_3$, $C_2H_5$, propyl, allyl or propargyl, $R^4$ is H and $R^3$ is $CH_3$, ethyl, propyl or allyl; or a pharmaceutically acceptable acid addition salt thereof.

Another more preferred embodiment is a compound of formula XXXXI wherein $R^1$ is $-CH_2-CH=CH_2$,

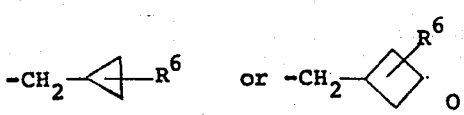

in which $R^6$ is H or $CH_3$, $R^2$ is H, $CH_3$,

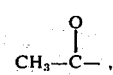

or

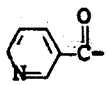

and $R^5$ is $CH_3$, $C_2H_5$, propyl, allyl or propargyl, $R^4$ is H and $R^3$ is $CH_3$; or a pharmaceutically acceptable acid addition salt thereof.

A still more preferred embodiment is a compound of formula XXXXI wherein $R^1$ is

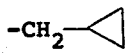

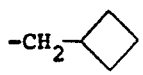

or $-CH_2-CH=CH_2$, $R^2$ is H, $CH_3$ or

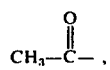

$R_5$ is methyl, $R^4$ is H and $R^3$ is allyl; or a pharmaceutically acceptable acid addition salt thereof.

Most preferred embodiments are:
A. (±)-5-Allyl-2-cyclobutylmethyl-2'-hydroxy-9β-methoxy-6,7-benzomorphan; or a pharmaceutically acceptable acid addition salt thereof.
B. (−)-5-Allyl-2-cyclobutylmethyl-2'-hydroxy-9β-methoxy-6,7-benzomorphan; or the hydrochloride, fumarate or tartrate salt thereof.
C. (±)-5-Allyl-2-cyclobutylmethyl-2'-hydroxy-9β-methoxy-9α-methyl-6,7-benzomorphan; or a pharmaceutically acceptable acid addition salt thereof.
D. (−)-5-Allyl-2-cyclobutylmethyl-2'-hydroxy-9β-methoxy-9α-methyl-6,7-benzomorphan; or the hydrochloride, fumarate or tartrate salt thereof.

The present invention provides a novel process for the preparation of the compound having the formula

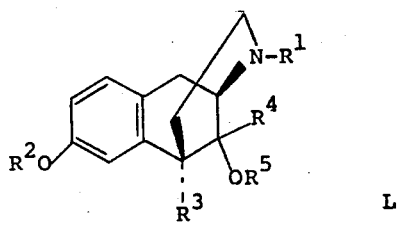

wherein $R^1$ is $-CH_2-C\equiv CH$, $-CH_2-CH=CH_2$,

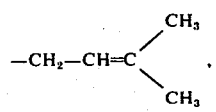

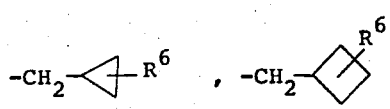

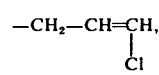

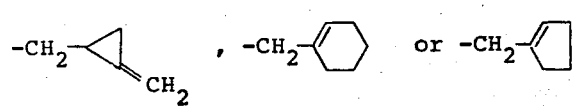

in which $R^6$ is H or $CH_3$; $R^2$ is H, lower alkyl, lower alkanoyl,

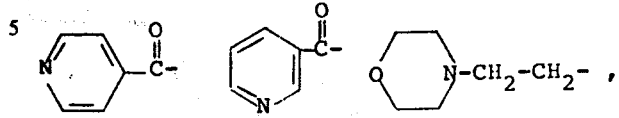

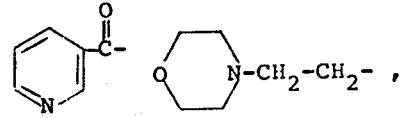

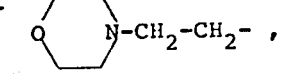

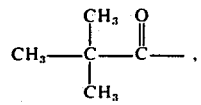

$CH_3O-CH_2-$ or

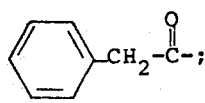

$R^5$ is lower alkyl, allyl or propargyl; $R^4$ is H or lower alkyl; and $R^3$ is lower alkyl or lower alkenyl; or a pharmaceutically acceptable acid addition salt thereof characterized in that a. a compound of the formula

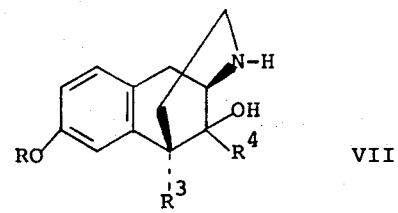

VII wherein R is a hydroxy blocking group and $R^3$ and $R^4$ are as defined above, is reacted to substitute the ring nitrogen with an electron withdrawing blocking group that prevents amine quaternarization;

b. the resultant blocked compound is treated with strong base, preferably an alkali metal hydride, then alkylated to produce the corresponding 9 $-OR^5$ substituted compound wherein R, $R^3$, $R^4$ and $R^5$ are as defined above, or treating the blocked compound with a diazo(lower)alkane or tri-(lower)alkyloxonium fluoroborate to alkylate the 9—OH function;

c. and when the electron withdrawing blocking group on the ring nitrogen is a functional group other than a group consisting of

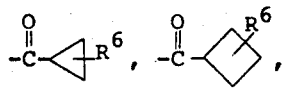

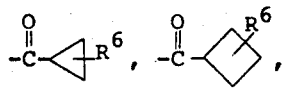

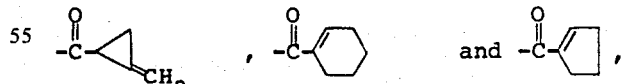

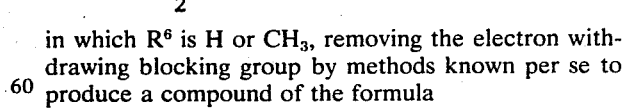

in which $R^6$ is H or $CH_3$, removing the electron withdrawing blocking group by methods known per se to produce a compound of the formula

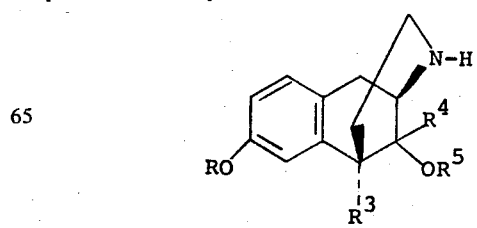

wherein R, R³, R⁴ and R⁵ are as defined above, then acylating or alkylating the >NH function by methods known per se to produce a compound of the formula

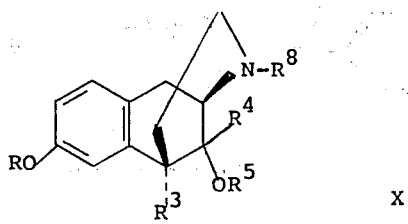

wherein

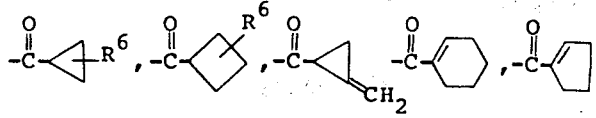

$-CH_2-C\equiv CH$, $-CH_2-CH=CH_2$,

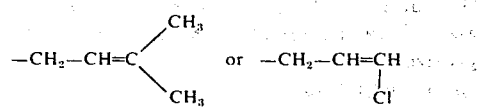

d. and, when R⁸ is a radical containing a carbonyl function, reducing the carbonyl function to a methylene by treatment with a reducing agent, preferably lithium aluminum hydride, whereby a compound of the formula

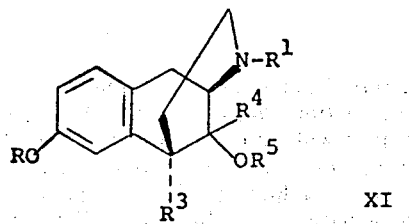

wherein R, R¹, R³, R⁴ and R⁵ are as defined above is produced;

e. then cleaving the hydroxy blocking group R by methods known per se to produce the compound of the formula L wherein R² is hydrogen;

f. then optionally reacting the 2'-hydroxy function by methods known per se to produce the corresponding compound of the formula L wherein R² is selected from the group consisting of lower alkyl, lower alkanoyl,

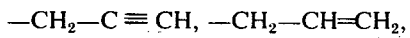

$CH_3O-CH_2-$ and

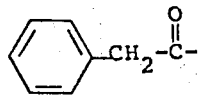

g. and if the compound L is a racemic mixture, optionally resolving compound L into its optical isomers by methods known per se.

h. and when an acid addition salt of the compound of formula L is desired, reacting said compound of formula L with a pharmaceutically acceptable acid according to methods known per se;

In step (a), the secondary amine ring nitrogen is preferably reacted with an electron withdrawing blocking group selected from the group consisting of

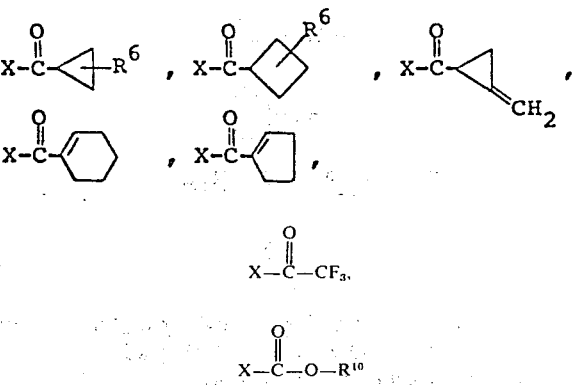

and X-CN, in which R⁶ is H or methyl, X is chloro, bromo or iodo and R¹⁰ is lower alkyl, or a functional equivalent thereof such as an anhydride, or the like. Additionally, the reaction is preferably conducted in a reaction-inert solvent such as benzene, xylene, chloroform, methylene chloride, ether and the like, with or without the aid of heat.

Preferably, in step (b), the ring nitrogen blocked compound is treated with a strong base, preferably an alkali metal hydride, and most preferably sodium hydride, in a ratio of about 1 to 1.1 mole of base per mole of blocked nitrogen compound, in a reaction-inert solvent such as dimethylformamide, dimethylacetamide, tetrahydrofuran, hexamethylphosphoramide, benzene, toluene, diethylether and the like, following which an excess of a di(lower)alkylsulfate, a (lower)alkyltosylate a (lower)alkyl halide, an allyl halide or a propargyl halide, in which halide is Br, Cl or iodo, but preferably methyl iodide, is added to produce the 9—OR⁵ function in which R⁵ is (lower)alkyl, allyl or propargyl; or alternatively the ring nitrogen blocked compound is treated with an excess of a diazo (lower)alkyl or a tri (lower)alkoxonium fluoroborate, but most preferably diazomethane, to produce the 9—OR⁵ function in which R⁵ is (lower)alkyl.

In step (c), when the ring nitrogen blocking group is other than one desired, it is removed by methods generally known in the art. For example, when the blocking group is a carbalkoxy or trifluoroacetyl group, the compound is preferably hydrolyzed with a strong alkali metal base, preferably potassium hydroxide, in a (lower)alkanol, preferably 95% ethanol, to produce the deblocked secondary ring amine. When the blocking group is a cyano group, the compound is preferably treated with lithium aluminum hydride in tetrahydrofuran with refluxing following which the mixture is treated with water and sodium hydroxide to produce the deblocked secondary amine.

After the ring nitrogen blocking group is removed, the secondary amine compound is then acylated preferably with an acid halide, anhydride or mixed anhydride of a compound selected from the group consisting of

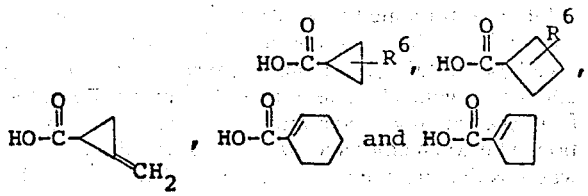

in a reaction-inert organic solvent such as methylene chloride, chloroform, diethyl ether and the like, with or without the aid of heat, in the presence of a tertiary amine; or the secondary amine is alkylated preferably with a compound selected from the group consisting of $X-CH_2-C \equiv CH$, $X-CH_2-CH=CH_2$,

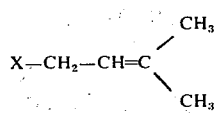

and

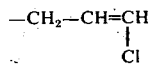

in which X is chloro, bromo or iodo, in a reaction-inert organic solvent, preferably a (lower)alkanol, to produce the compound having formula X.

In step (d), when $R^8$ is a radical containing a carbonyl function, the carbonyl function is preferably reduced to a methylene by treatment with lithium aluminum hydride, in a reaction-inert organic solvent such as diethyl ether, tetrahydrofuran, dioxane, and the like, and most preferably with the aid of heat, to produce compound XI.

In step (e), the hydroxy protecting group R is cleaved from the compound of formula XI by methods commonly known to the art. However, when R is lower alkyl, the R group is preferably selectively cleaved by treating the compound XI with sodium thioethoxide, boron tribromide, pyridine hydrochloride or hydrobromic acid in an appropriate solvent as is known in the art. Most preferably, the hydroxy protecting group R is cleaved by reaction with sodium thioethoxide in dimethylformamide to produce the compound L in which $R^2$ is H. When R is acyl or alkanoyl, R is most preferably removed by hydrolysis.

In step (f), the 2'-hydroxy function of compound L is preferably esterified or etherified by methods commonly known to the art. When it is desired to esterify the 2'-hydroxy function, compound L in which $R^2$ is H is preferably treated with an equimolar quantity of an acid halide, e.g., 4-nicotinoyl chloride, in the presence of a tertiary amine, such as pyridine, to produce the desired 2'-ester of compound L.

When it is desired to etherify the 2'-hydroxy function, compound L in which $R^2$ is H is preferably treated with an equimolar quantity of sodium hydride in dry dimethylformamide. An equimolar quantity of an appropriate halide, e.g., chloromethylmethyl ether, is added, followed by the addition of excess sodium carbonate, to produce the desired 2'-ester of compound L.

In step (h), the preparation of an acid addition salt of compound L is preferably accomplished in a manner similar to that described in examples 67 and 76.

The compounds of the present invention and certain intermediates therefore exist in the form of optical isomers, e.g., dextrorotatory, levorotatory and racemic mixtures. These compounds are represented by formulas L, XXXX, XXXXI, V, VI, VII, IX, X, XI and XII. It should be clearly understood that these intermediates and final products can be resolved as called for by optional step (g) at any time in the process or compounds L can be resolved at the end of the process by those methods commonly known in the art. If one starts with the levorotatory form of compound VII at the start of the process, then levorotatory compound L will be produced by the above described process.

The present invention further provides a novel process for the preparation of the compound having the formula

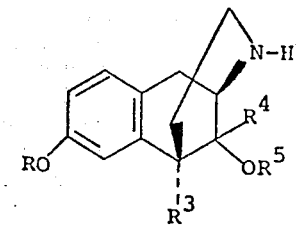

wherein R is a hydroxy blocking group, preferably lower alkyl, most preferably methyl; $R^5$ is lower alkyl, allyl or propargyl; $R^4$ is H or lower alkyl; and $R^3$ is lower alkyl or lower alkenyl; or an acid addition salt thereof characterized in that a. a compound of the formula

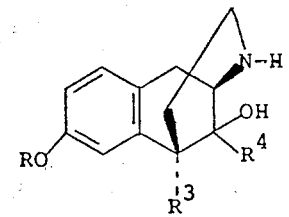

VII wherein R, $R^3$ and $R^4$ are as defined above, is reacted to substitute the ring nitrogen with an electron withdrawing blocking group that prevents amine quaternarization;

b. the resultant blocked compound is treated with strong base, preferably an alkali metal hydride, then alkylated to produce the corresponding 9 —$OR^5$ substituted compound wherein R, $R^3$, $R^4$ and $R^5$ are as defined above, or treating the blocked compound with a diazo(lower)alkane or tri- (lower)alkyloxonium fluoroborate to alkylate the 9—OH function;

c. and removing the electron withdrawing blocking group by methods known per se to produce such compound of the formula

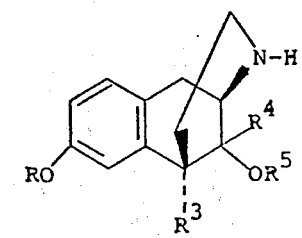

EXAMPLE 1

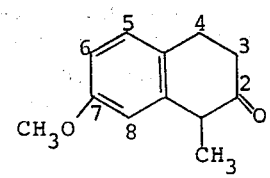

IIa

3,4-Dihydro-7-methoxy-1-methyl-2(1H)naphthalenone (IIa).

To a stirred solution of 50 g. (0.284 mole) of I (3,4-dihydro-7-methoxy-2(1H)naphthalenone) dissolved in 200 ml. of dry benzene was added during 5–10 minutes and under nitrogen, 40.5 g. (0.5 mole) of pyrrolidine dissolved in 50 ml. of benzene. The mixture was refluxed for one hour and 5 ml. of water was collected in a Dean-Stark apparatus. The mixture was cooled and added slowly to 0.5 mole of methyl iodide dissolved in 300 ml. of benzene. The resulting mixture was refluxed for three hours. Then 200 ml. of water was added to the reaction and refluxing was resumed. After 30 minutes, the mixture was cooled, the benzene layer was separated, washed with water, saturated with sodium bisulfite, dried, and evaporated to dryness. The residue was distilled to give IIa. The infrared (IR) and Nuclear Magnetic Resonance (NMR) spectra were consistent with the structure.

EXAMPLE 2

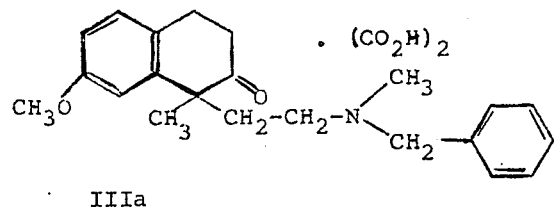

IIIa 1-(2-Benzylmethylaminoethyl)-7-methoxy-1-methyl-3,4-dihydro-2(1H)naphthalenone hydrogen oxalate (IIIa)

A solution of 7-methoxy-1-methyl-3,4-dihydro-2(1H)naphthalenone (0.12 m) IIa in benzene (40 ml) was added to a refluxing suspension of sodium hydride (0.14 m) in benzene (100 ml). After one hour reflux, this mixture was treated with a solution of 2-benzylmethylaminoethylchloride (0.12 m) in benzene (100 ml) and heated at reflux for 18 hrs. The reaction mixture was washed with water, then extracted into dilute hydrochloric acid. Neutralization of the acid extract with ammonium hydroxide and extraction with ether afforded an oil which was converted to an oxalate salt (78%); m.p. 137°–139°C.

Anal. calcd. for $C_{22}H_{27}NO_2 \cdot C_2H_2O_4$: C, 67.43; H, 6.84; N, 3.28. Found: C, 67.25; H, 7.05; N, 3.50.

EXAMPLE 3

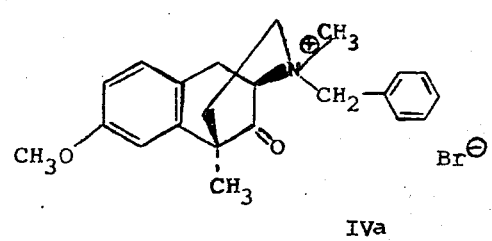

IVa

2-Benzyl-2'-methoxy-5-methyl-9-oxo-6,7-benzomorphan methobromide (IVa).

Compound IIIa was converted to its hydrobromide salt by treatment with sodium hydroxide solution, isolation by extraction with ether and subsequent treatment with HBr. This hydrobromide salt (0.21 m) was dissolved in 450 ml acetic acid and slowly treated with a solution of bromine (11.2 ml) in 50 ml acetic acid and stirred for ½ hr. This was diluted with two liters of "Skellysolve B" (essentially n-hexane) and cooled under nitrogen. The Skellysolve B layer was decanted from the gummy precipitate. This residue was partitioned between ether and water. This two phase system was basified with conc. ammonium hydroxide. The layers were immediately separated and the aqueous layer extracted with ether. Concentration of the ether extracts gave an oil. This oil was taken up in acetone and stirred several hours to give IVa as a crystalline solid (76%).

EXAMPLE 4

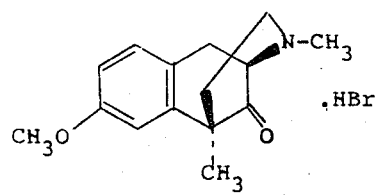

Va 2,5-Dimethyl-2'-methoxy-9-oxo-6,7-benzomorphan (Va).

Reduction of IVa in acetic acid using hydrogen and 10% palladium on carbon produced compound Va hydrobromide in 92% yield; m.p. 145°–149°C. This compound is a known compound [E. L. May and coworker, J. Org. Chem. 25, 1386 (1960)]. This synthesis represents an improved process for the preparation of these compounds.

EXAMPLE 5

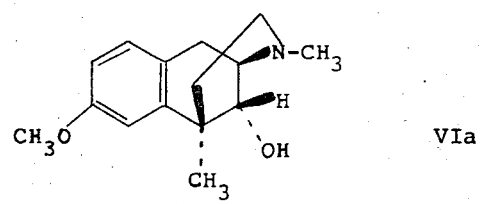

VIa 2,5-Dimethyl-9α-hydroxy-2'-methoxy-6,7-benzomorphan (VIa).

A mixture of 2,5-dimethyl-2'-methoxy-9-oxo-6,7-benzomorphan (V, 0.02 mole)[1] and 8 g cobaltous chloride hexahydrate in 100 ml 95% ethanol was warmed slightly to dissolve and then stirred for ½ hour at room temperature. Sodium borohydride (4g) was added portionwise with stirring under nitrogen. This dark mixture was stirred at room temperature under nitrogen for 18 hours. Seventy-five ml 6N hydrochloric acid was cautiously added and the ethanol was removed at reduced pressure. The resultant blue solution was basified with concentrated ammonium hydroxide and extracted with methylene chloride. Drying and concentration of the extracts gave 4.9 g of crystalline material which glc (gas-liquid chromatography) analysis indicated to be 88% α-hydroxy and 9% β-hydroxy isomers. Crystallization from ethyl acetate-Skellysolve B (essentially n-hexane) gave the pure α isomer (VIa); m.p. 115.0° –116.5°C (lit.[2] mp 115.5° –117°C).

[1]J. G. Murphy, J. H. Ager and E. L. May, J. Org. Chem., 25, 3386 (1960).
[2]H. Kugita and E. L. May, J. Org. Chem., 26 1954 (1961).

EXAMPLE 6

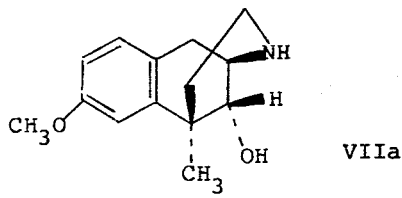

VIIa

9α-Hydroxy-2'-methoxy-5-methyl-6,7-benzomorphan (VIIa) hydrogen oxalate

Compound VIa (0.014 moles) was acetylated with acetic anhydride (50 ml) at steam bath temperature for 2 hrs. to give the 9α-acetoxy compound. This material was taken up in benzene (75 ml), treated with potassium carbonate (2 g) and ethyl chloroformate (5 ml) and heated at reflux for 18 hours. The resultant mixture was washed with water, dilute hydrochloric acid and saturated sodium chloride. The aqueous layers were extracted twice more with benzene. The benzene layers were dried ($K_2CO_3$) and concentrated to give 9α-acetoxy-2-carbethoxy-2'-methoxy-5-methyl-6,7-benzomorphan. This material was hydrolyzed with potassium hydroxide 25 g--85% pellets) in refluxing 95% ethanol (125 ml) for 66 hours. The ethanol was removed at reduced pressure. The residue was treated with dilute sodium bicarbonate and extracted with methylene chloride to give the product (VIIa) which was converted to its hydrogen oxalate salt in 95% ethanol (89% yield); m.p. 212°–215°C.

Anal. calc'd. for $C_{14}H_{19}NO_2.C_2H_2O_4$: C, 59.43; H, 6.55; N, 4.33. Found: C, 59.58; H, 6.31; N, 4.44

EXAMPLE 7

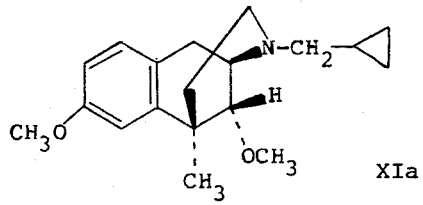

XIa

2-Cyclopropylmethyl-2',9α-dimethoxy-5-methyl-6,7-benzomorphan (XIa) hydrochloride.

Compound VIIa free base (0.015 moles) in methylene chloride (50 ml) and triethylamine 8 ml) was treated with cyclopropylcarbonyl chloride (2.3 ml) under nitrogen. This was stirred for 1 hour and then treated with methanol (7 ml) and stirred for 5 minutes and concentrated to dryness. The residue was taken up in toluene and washed with dilute hydrochloric acid, water and saturated sodium carbonate. Drying and concentration of the toluene extracts gave 2-cyclopropylcarbonyl-2'-methoxy-9α-hydroxy-5-methyl-6,7-benzomorphan [IXa, approximately 100% yield - >98% purity by GLC analysis]. A solution of IXa in dimethylformamide (25 ml) was added to a suspension of NaH (0.015 m) in dimethylformamide (10 ml) under nitrogen. After ½ hour, methyl iodide was added in two portions one hour apart (1 ml each time) and the mixture was stirred for an additional 16 hours. After removal of the solvent at reduced pressure, the residue was treated with water and extracted with methylene chloride to give 2-cyclopropylcarbonyl-2', 9α-dimethoxy-5-methyl-6,7-benzomorphan [Xa, approximately 100% yield of ≈98% purity by GLC analysis]. This material was reduced with $LiAlH_4$ in tetrahydrofuran for 16 hours to give the title product, which was isolated as the crystalline hydrochloride salt (1.4 g, 85% yield); m.p. 230°–233°C.

Anal. calc'd. for $C_{19}H_{27}NO_2.HCl$: C, 67.54; H, 8.35; N, 4.15. Found: C, 67.58; H, 8.46; N, 4.36

EXAMPLE 8

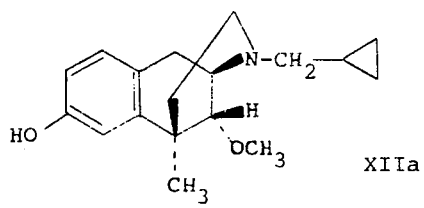

XIIa

2-Cyclopropylmethyl-2'-hydroxy-9α-methoxy-5-methyl-6,7-benzomorphan (XIIa).

A mixture of compound XIa (0.0028 moles) and sodium thioethoxide (0.05 m, prepared from sodium hydride and ethyl mercaptan) in dimethylformamide (80 ml) was heated at reflux for 3 hours. The solvent was removed at reduced pressure. The residue was treated with toluene and extracted with dilute hydrochloric acid. The acid extracts were basified ($Na_2CO_3$) and extracted with methylene chloride to give XIIa which was crystallized from acetonitrile; m.p. 188°–189°C.

Anal. calc'd. for $C_{18}H_{25}NO_2$: C, 75.22; H, 8.77; N, 4.87. Found: C, 75.31; H, 8.85; N, 5.18.

EXAMPLE 9

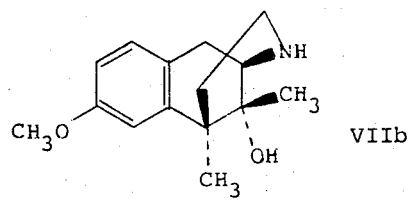

VIIb 5,9β-Dimethyl-9α-hydroxy-2'-methoxy-6,7-benzomorphan (VIIb) fumarate.

A refluxing mixture of 9α-hydroxy-2'-methoxy-2,5,9β-trimethyl-6,7-benzomorphan[0.032 m, the compound prepared and reported by May et al in J.

Org. Chem. 26, 188 (1961)] and potassium carbonate (26 g) in benzene (150 ml) was treated with a solution of trichloroethyl chloroformate (0.095 m) in benzene (100 ml). After heating at reflux for 60 hours, this mixture was treated with water (200 ml) and stirred for ½ hour. The benzene layer was separated, washed with saturated sodium chloride, dried (MgSO₄) and concentrated to give crude 2-trichlorocarbethoxy-5,9β-dimethyl-9α-hydroxy-2-methoxy-6,7-benzomorphan. This material was taken up in acetic acid (100 ml) and added to a suspension of zinc (40 g) in acetic acid (100 ml) under nitrogen over a period of ½ hour. After the addition was completed, more zinc (20 g) was added and stirring was continued for 1 hour. The zinc was removed by filtration and the filtrate concentrated. The residue was treated with dilute ammonium hydroxide and extracted several times with chloroform to give material VIIb which was converted to a fumarate salt by reaction with fumaric acid (3.9 g) in n-propanol; m.p. >250° C.

Anal. calc'd. for $C_{15}H_{21}NO_2 \cdot \frac{1}{2}C_4H_4O_4$: C, 66.86; H, 7.59; N, 4.59. Found: C, 66.92; H, 7.83; N, 4.66.

EXAMPLE 10

2-Cyclopropylcarbonyl-5,9β-dimethyl-9α-hydroxy-2'-methoxy-6,7-benzomorphan (IXb).

A solution of (0.012 m) VIIb (free base) in methylene chloride (30 ml) and triethylamine (4 ml) was treated with a solution of cyclopropylcarbonyl chloride (0.02 m) in methylene chloride (20 ml). After a few hours stirring at room temperature, this mixture was washed with dilute hydrochloric acid, water and dilute sodium carbonate. Drying (MgSO₄) and concentration of the organic extracts gave material IXb which was crystallized from 95%-ethanol.

EXAMPLE 11

2-Cyclopropylmethyl-2',9α-dimethoxy-5,9β-dimethyl-6,7-benzomorphan (XIb) fumarate.

A solution of IXb (0.00635 m) in dimethylformamide (30 ml) was treated with sodium hydride (760 mg of 60% dispersion in mineral oil) with stirring under nitrogen. After ½ hour methyl iodide (1 ml) was added and stirring continued. Another portion of methyl iodide (1 ml) was added one hour later and stirring continued for 18 hours. A few drops acetic acid were added and the dimethylformamide was removed at reduced pressure. The residue was treated with water and extracted with methylene chloride to give 2-cyclopropylcarbonyl-2',9α-dimethoxy-5,9β-dimethyl-6,7-benzomorphan (Xb) contaminated with mineral oil. The mineral oil was removed by treatment with n-pentane and extraction with acetonitrile to give Xb (96% pure by GLC). Material Xb was reduced with LiAlH₄ (720 mg) in tetrahydrofuran (40 ml) for 18 hours to give XIb which forms a crystalline hydrogen fumarate, (2.1 g, 78% yield); m.p. 154°–155°C.

Anal. calc'd. for $C_{20}H_{29}NO_2 \cdot C_4H_4O_4$: C, 66.80; H, 7.71; N, 3.25. Found: C, 66.54, 66.44; H, 7.86, 8.00; N, 3,73, 3.43.

EXAMPLE 12

2-Cyclopropylmethyl-5,9β-dimethyl-2'-hydroxy-9α-methoxy-6,7-benzomorphan (XIIb) fumarate.

Substitution in the procedure of example 8 for the compound XIa used therein of an equimolar quantity of compound XIb produced the title compound XIIb as a hydrogen fumarate; m.p. 191°–194°C.

Anal. calc'd. for $C_{19}H_{27}NO_2 \cdot C_4H_4O_4$: C, 66.16; H, 7.48; N, 3.36. Found: C, 65.63; H, 7.76; N, 3.01; H₂O, 0.35.

EXAMPLE 13

2-Cyclobutylmethyl-2',9α-dimethoxy-5,9β-dimethyl-6,7-benzomorphan (XIc) fumarate.

A. Substitution in the procedure of example 10 for the cyclopropylcarbonyl chloride used therein of an equimolar quantity of cyclobutylcarbonyl chloride produced 2-cyclobutylcarbonyl-5,9β-dimethyl-9α-hydroxy-2'-methoxy-6,7-benzomorphan (IXc).

B. Substitution in the procedure of example 11 for the compound IXb used therein of an equimolar quantity of IXc produced the title product XIc as the 3/2 fumarate salt; m.p. 150°–151°C.

Anal. calc'd. for $C_{21}H_{31}NO_2 \cdot 3/2(C_4H_4O_4)$: C, 64.39; H, 7.41; N, 2.78. Found: C, 64.24; H, 7.70; N, 2.61.

EXAMPLE 14

2-Cyclobutylmethyl-5,9β-dimethyl-2'-hydroxy-9α-methoxy-6,7-benzomorphan (XIIc) fumarate.

Substitution in the procedure of example 8 for the compound XIa used therein of an equimolar quantity of compound XIc produced the title compound XIIc which was isolated as the hydrobromide salt; m.p. 223°–226°C.

Anal. Calc'd. for $C_{20}H_{29}NO_2 \cdot HBr$: C, 60.60; H, 7.63; N, 3.53. Found: C, 60.40; H, 7.54; N, 3.54.

The hydrobromide and hydrochloride salts are prepared by dissolving the amine in a minimum quantity of absolute ethanol to which is slowly added an anhydrous ethanolic solution of HBr or HCl previously prepared by pumping HBr or HCl gas into ethanol. The salt is precipitated by slowly adding diethyl ether with scratching. The salt is collected by filtration and purified by recrystallization.

EXAMPLE 15

Resolution of (±)-2,5-Dimethyl-2'-methoxy-9-oxo-6,7-benzomorphan (Va).

A.

(+)-2,5-Dimethyl-2'-methoxy-9-oxo-6,7-benzomorphan (+)-hydrogen tartrate.

A mixture of Va(racemic) (0.072 m) and (+)-tartaric acid (0.072 m) was taken up in 150 ml water and 30 ml 95% ethanol, filtered and concentrated to 150 ml and stored at 0°–5° for crystallization. The crystals were collected, washed with 95% ethanol and recrystallized from 50% aqueousethanol to give 10.1 g (66%) (+)-2,5-dimethyl-2'-methoxy-9-oxo-6,7-benzomorphan (+) hydrogen tartrate dihydrate.

Anal. calc'd. for $C_{15}H_{19}NO_2 \cdot C_4H_6O_6 \cdot 2 H_2O$: C, 52.89; H, 6.78; N, 3.25; H₂O, 8.3 Found: C, 52.89; H, 7.07; N, 3.17; H₂O, 8.94.

The free base was isolated by dissolving the tartrate in water and making the solution basic with sodium carbonate. The mixture was extracted with methylene chloride, washed with water, dried over anhydrous sodium sulfate, filtered and taken to dryness in vacuo. The rotation of the free base is $[\alpha]_D^{21} + 86.5°$ (c 1.038, 95% ethanol).

B.
(−)-2,5-Dimethyl-2′-methoxy-9-oxo-6,7-benzomorphan (−) hydrogen tartrate.

The first mother liquor from the (+) isomer above was basified with sodium carbonate and extracted with methylene chloride to give an oil (10.3 g). This oil was treated with (−)-tartaric acid (6.5 g) and taken up in 100 ml water and 30 ml 95% ethanol (hot), filtered, concentrated to about 100 ml and cooled at 0°–5°C for crystallization. The crystals were collected and recrystallized from 100 ml 50% aqueous-ethanol to give 10.6 g (68%) (−)-2,5-dimethyl-2′-methoxy-9-oxo-6,7-benzomorphan (−)hydrogen tartrate; m.p. 157.5°–158.5°C, $[\alpha]_D^{22} -48.5°$ (c 1.047, water).

Anal. calc'd. for $C_{15}H_{19}NO_2 \cdot C_4H_6O_6 \cdot 2H_2O$: C, 52.89; H, 6.78; N, 3.25; $H_2O$, 8.35. Found: C, 52.17; H, 6.99; N, 3.00, $H_2O$, 9.10.

The free base was isolated as in A supra and the optical rotation was $[\alpha]_D^{22} - 85.5°$ (c 1.054, 95% ethanol).

EXAMPLE 16

(−)-2,5-Dimethyl-9α-hydroxy-2′-methoxy-6,7-benzomorphan [(−)-VIa].

(−)-2,5-Dimethyl-2′-methoxy-9-oxo-6,7-benzomorphan [free base, 0.0765 m] was hydrogenated on a Parr shaker in 250 ml 95% ethanol using 150 mg platinum oxide as a catalyst. The theoretical uptake was observed after 1½ hours. The catalyst was removed by filtration and the filtrate concentrated to dryness to give a crystalline residue which was recrystallized from toluene to give pure title product (18.2g--96%); m.p. 146.5°–148°C., $[\alpha]_D^{21} - 56.5°$ (c 1.022, 95% ethanol). GLC indicates one pure compound (α-isomer only).

Anal. calc'd. for $C_{15}H_{21}NO_2$: C, 72.84; H, 8.56; N, 5.66. Found: C, 73.29; H, 8.62; N, 5.66.

EXAMPLE 17

(−)9α-Hydroxy-2′-methoxy-5-methyl-6,7-benzomorphan [(−)-VIIa].

A mixture of (−)-VIa (0.033 m) and potassium carbonate (16.5 g) in toluene (160 ml) was treated with trichloroethyl chloroformate (16.5 ml) with stirring. This mixture was heated at reflux under nitrogen for 18 hours. After cooling, the mixture was treated with 100 ml water and the layers separated. The aqueous layer was extracted again with toluene. The toluene extracts were washed (saturated sodium chloride), dried ($K_2CO_3$) and concentrated. The residue was taken up in methanol (120 ml)-water (12 ml), cooled, treated with potassium hydroxide (12 g) and stirred at 0°–5°C for 45 minutes. Acetic acid (12 ml) was added and the solution concentrated. The residue was treated with dilute hydrochloric acid and extracted with toluene to give (−)-2-trichlorocarbethoxy-9α-hydroxy-2′-methoxy-5-methyl-6,7-benzomorphan. This material was taken up in 100 ml acetic acid and added slowly to a warm suspension of zinc dust (15 g) in 50 ml acetic acid under nitrogen. After the initial reaction had subsided, the mixture was heated at reflux for ½ hour. The zinc was removed by filtration (under nitrogen) and the filtrate concentrated. Treatment of the residue with dilute ammonium hydroxide and extraction with chloroform gave (−)-VIIa (8g - 100%) which glc indicated to be ~97% pure. This material forms a crystalline hydrochloride salt; m.p. >250°C, $[\alpha]_D^{21} - 29.6°$ (c 1.015, 95% ethanol).

Anal. calc'd. for $C_{14}H_{19}NO_2 \cdot HCl$: C, 62.33; H, 7.47; N, 5.19. Found: C, 62.31; H, 7.22; N, 5.56.

EXAMPLE 18

(−)-2-Cyclopropylmethyl-2′-9α-dimethoxy-5-methyl-6,7-benzomorphan [(−)-XIa].

Substitution in the procedure of example 7 for the VIIa used therein of an equimolar quantity of (−)-VIIa produced the title product (−)-XIa in 92% yield after purification by chromatography on alumina (elution with benzene-ether). Toluene was used in the first reaction step instead of methylene chloride. The product was crystallized as the oxalate salt; m.p. 185.5°–186.5 C., $[\alpha]_D^{20} - 48.9°$(c 0.066, 95% ethanol).

Anal. calc'd. for $C_{19}H_{27}NO_2 \cdot C_2H_2O_4$: C, 64.43; H, 7.47; N, 3.58. Found: C, 64.32; H, 7.31; N, 3.70.

EXAMPLE 19

(−)-2-Cyclopropylmethyl-2′-hydroxy-9α-methoxy-5-methyl-6,7-benzomorphan [(−)-XIIa].

Substitution in the procedure of example 8 for the XIa used therein of an equimolar quantity of (−)-XIa produced the title compound; m.p. 180.0° - 180.5°C.

Anal. calc'd. for $C_{18}H_{25}NO_2$: C, 75.22; H, 8.77; N, 4.87. Found: C, 75.62; H, 8.50; N, 4.69.

(−)-XIIa forms a crystalline fumarate salt, m.p. 179.0°–180.0°C., $[\alpha]_D^{20} - 57.4°$ (c 1.011, 95% ethanol).

Anal. calc'd. for $C_{18}H_{25}NO_2 \cdot ½(C_4H_4O_4)$: C, 69.54; H, 7.88; N, 4.06. Found: C, 69.70; H, 7.87; N, 3.78.

EXAMPLE 20

(+)-2-Cyclopropylmethyl-2′-hydroxy-9α-methoxy-5-methyl-6,7-benzomorphan [(+)-XIIa].

Successive substitution in the procedures of examples 16–19 for the levorotatory isomer used therein of an equimolar quantity of the dextrorotatory isomer (+)-VIa produces the title product, (+)-XIIa; m.p. as the (l) tartrate salt was 147.0°–148.0°C;$[\alpha]_D^{20} + 37.3°$ (C 1.002, 95% ethanol).

Anal.Calc'd. for $(C_{18}H_{25}NO_2)_2 \cdot C_4H_6O_6 \cdot H_2O$: C, 64.67; H, 7.87; N, 3.77; $H_2O$, 2.42 Found C, 64.14; H, 7.68; N, 4.10; $H_2O$, 3.14.

EXAMPLE 21

2-Cyclopropylmethyl-9α-ethoxy-2′-methoxy-5-methyl-6,7-benzomorphan (XId).

Substitution in the procedure of example 7 for the methyl iodide used therein of an equimolar quantity of ethyl iodide produced the title compound which was isolated as the hydrochloride salt; 83% yield; m.p. 236°–240°C.

Anal. calc'd. for $C_{20}H_{29}NO_2 \cdot HCl$: C, 68.26; H, 8.59; N, 3.98. Found: C, 68.65; H, 8.56; N, 4.13.

EXAMPLE 22

2-Cyclopropylmethyl-9α-ethoxy-2′-hydroxy-5-methyl-6,7-benzomorphan (XIId).

Substitution in the procedure of example 8 for the compound XIa used therein of an equimolar quantity of XId produced the title compound which was isolated as the hydrochloride salt containing one mole of acetone solvate; m.p. 136°–145°C.

Anal. calc'd. for $C_{19}H_{27}NO_2 \cdot HCl \cdot C_3H_6O$: C, 66.78; H, 8.60; N, 3.54. Found: C, 67.15; H, 8.60; N, 3.85.

EXAMPLE 23

9α-Allyloxy-2-cyclopropylmethyl-2'-methoxy-5-methyl-6,7-benzomorphan hydrochloride (XIe).

Substitution in the procedure of example 7 for the methyl iodide used therein of an equimolar quantity of allyl bromide produced the title compound as the hydrochloride salt; m.p. 222°–227°C.

Anal. Calc'd. for $C_{21}H_{29}NO_2 \cdot HCl$: C, 69.30; H, 8.31; N, 3.85. Found: C, 69.21; H, 8.38; N, 3.95.

EXAMPLE 24

9α-Allyloxy-2-cyclopropylmethyl-2'-hydroxy-5-methyl-6,7-benzomorphan (XIIe).

Substitution in the procedure of example 8 for the compound XIa used therein of an equimolar quantity of XIe produced the title compound which was isolated as a hydrochloride salt; m.p. 255°–260° C.

Anal. calc'.d for $C_{20}H_{27}NO_2 \cdot HCl$: C, 68.65; H, 8.07; N, 4.00. Found C, 68.39; H, 7.94; N, 4.22

EXAMPLE 25

2-Cyclopropylmethyl-2'-methoxy-5-methyl-9α-propargyloxy-6,7-benzomorphan (XIf)hydrochloride.

Substitution in the procedure of example 7 for the methyl iodide used therein of an equimolar quantity of propargyl bromide produces the title compound XI as the hydrochloride salt.

EXAMPLE 26

2-Cyclopropylmethyl-2'-hydroxy-5-methyl-9α-propargyloxy-6.7-benzomorphan (XIIF).

Substitution in the procedure of example 8 for the compound XIa used therein of an equimolar quantity of XIf produces the title compound XIIf.

EXAMPLE 27

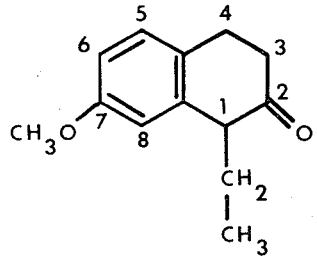

IIk 3,4-Dihydro-7-methoxy-1-ethyl-2(1H)naphthalenone (IIk).

To a stirred solution of 50 g. (0.284 mole) of Ia (3,4-dihydro-7-methoxy-2(1H)naphthalenone) dissolved in 200 ml. of dry benzene is added during 5–10 minutes and under nitrogen, 40.5 g. (0.5 mole) of pyrrolidine dissolved in 50 ml. of benzene. The mixture is refluxed for one hour and 5 ml. of water is collected in a Dean-Stark apparatus. The mixture is cooled and added slowly to 0.5 mole of ethyl iodide dissolved in 300 ml. of benzene. The resulting mixture is refluxed for three hours. Then 200 ml. of water is added to the reaction and refluxing is resumed. After 30 minutes the mixture is cooled, the benzene layer is separated, washed with water, saturated with sodium bisulfite and evaporated to dryness. The residue is distilled to give IIk.

EXAMPLE 28

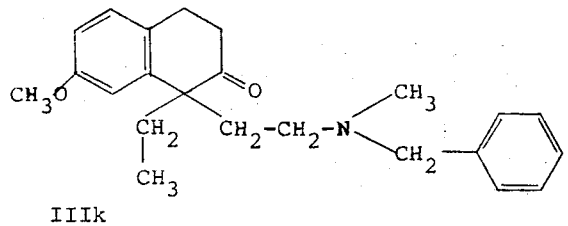

IIIk 1-(2-Benzylmethylaminoethyl)-7-methoxy-1-ethyl-3,4-dihydro2(1H)naphthalenone hydrogen oxalate (IIIk).

A solution of 7-methoxy-1-ethyl-3,4-dihydro-2(1H)naphthalenone (0.12 m) IIk in benzene (40 ml) is added to a refluxing suspension of sodium hydride (0.14 m) in benzene (100 ml). After one hour reflux, this mixture is treated with a solution of 2-benzylmethylaminoethylchloride (0.12 m) in benzene (100 ml) and heated at reflux for 18 hours. The reaction mixture is washed with water, then extracted into dilute hydrochloric acid. Neutralization of the acid extract with ammonium hydroxide and extraction with ether affords an oil which is converted to an oxalate salt (IIIk).

EXAMPLE 29

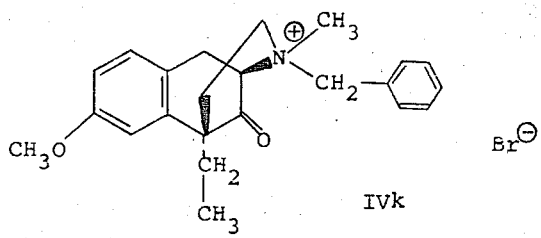

IVk

2-Benzyl-5-ethyl-2'-methoxy-9-oxo-6,7-benzomorphan methobromide (IVk).

Compound IIIk is converted to its hydrobromide salt by treatment with sodium hydroxide solution, isolation by extraction with ether and subsequent treatment with HBr. This hydrobromide salt is dissolved in acetic acid and slowly treated with a solution of bromine in 50 ml acetic acid and stirred for ½ hr. This is diluted with 2 liters of Skellysolve B (essentially n-hexane) and cooled under nitrogen. The Skellysolve B layer is decanted from the gummy precipitate. This residue is partitioned between ether and water. This two phase system is basified with conc. ammonium hydroxide. The layers are immediately separated and the aqueous layer extracted with ether. Concentration of the ether extracts give an oil. This oil is taken up in acetone and stirred several hours to give IVk as a crystalline solid.

EXAMPLE 30

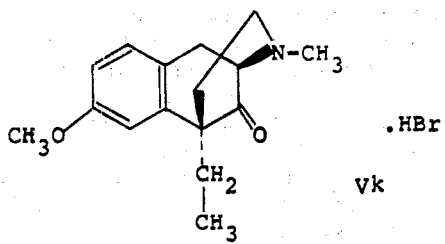

Vk · HBr

5-Ethyl-2'-methoxy-2-methyl-9-oxo-6,7-benzomorphan (Vk).

Reduction of IVk in acetic acid using hydrogen and 10% palladium on carbon produces compound Vk.

EXAMPLE 31

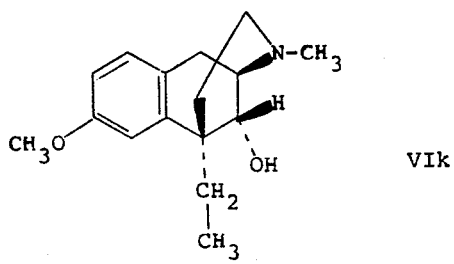

VIk

5-Ethyl-9α-hydroxy-2'-methoxy-2-methyl-6,7-benzomorphan (VIk).

A mixture of 5-ethyl-2'-methoxy-2-methyl-9-oxo-6,7-benzomorphan (V, 0.02 mole) and 8 g. cobaltous chloride hexahydrate in 100 ml 95% ethanol warmed slightly to dissolve and then stirred for ½ hour at room temperature. Sodium borohydride (4g) is added portionwise with stirring under nitrogen. This dark mixture is stirred at room temperature under nitrogen for 18 hours. Seventy-five ml 6N hydrochloric acid is cautiously added and the ethanol is removed at reduced pressure. The resultant blue solution is basified with concentrated ammonium hydroxide and extracted with methylene chloride. Drying and concentration of the extracts gives material determined by glc to be primarily the desired 9α-isomer (VIk).

EXAMPLE 32

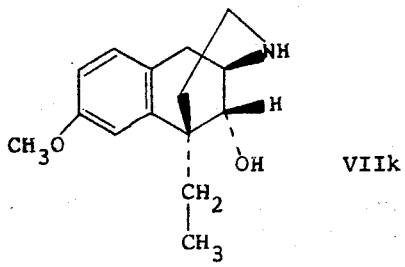

VIIk

5-Ethyl-9α-hydroxy-2'-methoxy-6,7-benzomorphan (VIIk) hydrogen oxalate.

Compound VIk (0.014 moles) is acetylated with acetic anhydride (50 ml) at steam bath temperature for 2 hours to give the 9α-acetoxy compound. This material is taken up in benzene (75 ml), treated with potassium carbonate (2 g) and ethyl chloroformate (5 ml) and heated at reflux for 18 hours. The resultant mixture is washed with water, dilute hydrochloric acid and saturated sodium chloride. The aqueous layers are extracted twice more with benzene. The benzene layers are dried (K₂CO₃) and concentrated to give 9α-acetoxy-2-carbethoxy-2'-methoxy-5-ethyl-6,7-benzomorphan. This material is hydrolyzed with potassium hydroxide (25 g—85% pellets) in refluxing 95% ethanol (125 ml) for 66 hours. The ethanol is removed at reduced pressure. The residue is treated with dilute sodium bicarbonate and extracted with methylene chloride to give the product (VIIk) which is converted to its hydrogen oxalate salt in 95% ethanol.

EXAMPLE 33

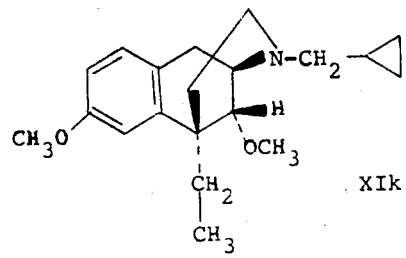

XIk

2-Cyclopropylmethyl-2',9α-dimethoxy-5-ethyl-6,7-benzomorphan (XIk) hydrochloride.

Compound VIIk free base (0.015 moles) in methylene chloride (50 ml) and triethylamine (8 ml) is treated with cyclopropylcarbonyl chloride (2.3 ml) under nitrogen. This is stirred for 1 hour and then treated with methanol (7 ml) and stirred for 5 minutes and concentrated to dryness. The residue is taken up in toluene and washed with dilute hydrochloric acid, water and saturated sodium carbonate. Drying and concentration of the toluene extracts gives 2-cyclopropylcarbonyl-2'-methoxy-9α-hydroxy-5-ethyl-6,7-benzomorphan [IXk]. A solution of IXk in dimethylformamide (25 ml) is added to a suspension of NaH (0.015 m) in dimethylformamide (10 ml) under nitrogen. After ½ hour, methyl iodide is added in two portions one hour apart (1 ml each time) and the mixture is stirred for an additional 16 hours. After removal of the solvent at reduced pressure, the residue is treated with water and extracted with methylene chloride to give 2-cyclopropylcarbonyl-2',9α-dimethoxy-5-ethyl-6,7-benzomorphan [Xk]. This material is reduced with LiAlH₄ in tetrahydrofuran for 16 hours to give the title product, which is isolated as the crystalline hydrochloride salt.

EXAMPLE 34

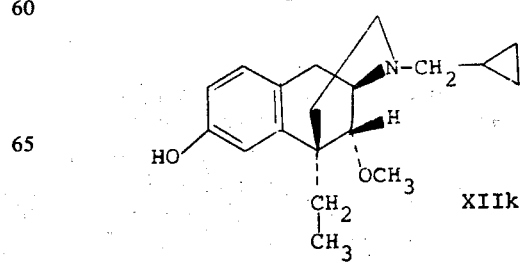

XIIk

2-Cyclopropylmethyl-2'-hydroxy-5-ethyl-9α-methoxy-6,7-benzomorphan (XIIk).

A mixture of compound XIk (0.0028 moles) and sodium thioethoxide (0.05 m, prepared from sodium hydride and ethyl mercaptan) in dimethylformamide (80 ml) is heated at reflux for 3 hours. The solvent is removed at reduced pressure. The residue is treated with toluene and extracted with dilute hydrochloric acid. The acid extracts are basified (Na$_2$CO$_3$) and extracted with methylene chloride to give XIIk which is crystallized from acetonitrile.

EXAMPLE 35

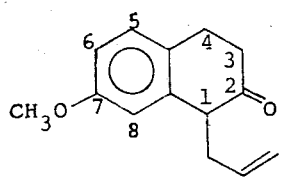

3,4-Dihydro-7-methoxy-1-allyl-2(1H)naphthalenone (IIm).

To a stirred solution of 50 g. (0.0284 mole) of Ia (3,4-dihydro-7-methoxy-2(3,4-dihydro-7-methoxy-2(1H)naphthalenone) dissolved in 200 ml. of dry benzene was added during 5–10 minutes and under nitrogen, 40.5 g. (0.5 mole) of pyrrolidine dissolved in 50 ml. of benzene. The mixture was refluxed for one hour and 5 ml. of water was collected in a Dean-Stark apparatus. The mixture was cooled and added slowly to 60.5 g. (0.5 mole) of allyl bromide dissolved in 300 ml. of benzene. The resulting mixture was refluxed for three hours. Then 200 ml. of water was added to the reaction and refluxing was resumed. After 90 minutes, the mixture was cooled, the benzene layer was separated, washed with water, followed by water saturated with sodium chloride, dried over sodium sulfate and evaporated to dryness. The residue was distilled to give 52.20 g. (85% yield) of IIm; b.p. 106°–112°/0.01–0.05 mm. The infrared (IR) and Nuclear Magnetic Resonance (NMR) spectra were consistent with the structure.

Anal. calc'd. for C$_{14}$H$_{16}$O$_2$: C, 77.74; H, 7.45. Found: C, 77.47; H, 7.50.

EXAMPLE 36

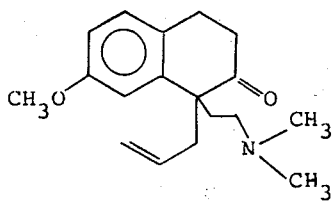

3,4-Dihydro-7-methoxy-1-allyl-1-(2-dimethylaminoethyl)-2(1H)naphthalenone hydrobromide (IIIm).

A mixture of 400 ml. dry benzene, 22 g. (0.25 mole) of tert.-amyl alcohol and 10.62 g (0.25 mole) of sodium hydride was refluxed under N$_2$ for 30 minutes or until all the hydride was consumed. Then 47.2 g. (0.22 mole) of IIm in 100 ml. of benzene was added slowly while distilling off the excess of amyl alcohol. Another 100 ml. of benzene was added and distilled off. Then 28 g. (0.3 mole) of 2-chloro-N,N-dimethylaminoethane in 100 ml. of benzene was added dropwise. The reaction mixture was refluxed for 20 hours, washed twice with water, and diluted with ether and extracted with 1N HCl. The acidic extract was warmed to 60° C. for 1 hour, cooled and extracted with ether to recover 15 g. of IIm. The acidic extract was then cooled, basified with NH$_4$OH and extracted with ether. It was dried over potassium carbonate, treated with charcoal and after filtration, with dry HBr. There was obtained 33.87 g. (61.5%) of HBr salt of IIIm. After recrystallization from methanol/ether, it melted at 139°–140°C. The IR and NMR were consistent with the structure.

Anal. calc'd for C$_{18}$H$_{25}$NO$_2$.HBr: C, 58.69; H, 7.11; N, 3.80. Found: C, 58.63; H, 7.16; N, 3.59.

EXAMPLE 37

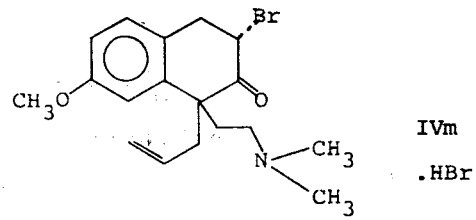

3-Bromo-3,4-dihydro-7-methoxy-1-allyl-1(2-dimethylaminoethyl-2-(1H)naphthalenone hydrobromide (IVm).

To a stirred solution of 15 g. (41 mmole) of IIIm in 100 ml. of methylene chloride and 300 ml. tetrahydrofuran (THF) in the dark, a solution of 20.58 g. (41.5 mmole) pyrrolidone hydrotribromide in 300 ml. of THF was added over a four hour period. After the addition, the reaction mixture was left overnight at room temperature. The solvents were evaporated to dryness and the solid residue recrystallized from 700 ml. of isopropanol to give 12.7 g. (68.5%) of IVm; m.p. 149°–150° C. The IR and NMR were consistent with the structure.

Anal. calc'd. for C$_{18}$H$_{24}$NO$_2$Br.HBr: C, 48.34; H, 5.63; N, 3.13. Found: C, 48.64; H, 5.70; N, 3.14.

EXAMPLE 38

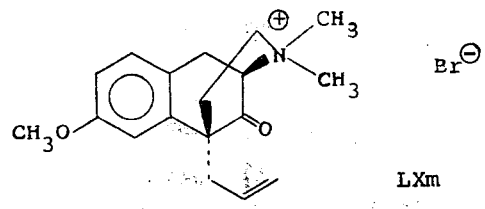

5-Allyl-2'-methoxy-2-methyl-9-oxo-6,7-benzomorphan methobromide (LXm).

The HBr salt IVm (12.6 g., 0.028 mole) was dissolved in ice cold water, placed in a separatory funnel and covered with ether. Enough concentrated ammonium hydroxide was added to alkalinize the mixture

37 and the free base of IVm was extracted and separated as rapidly as possible. The ether was evaporated, and the residue was dissolved in acetone and left overnight. There was obtained 6.55 g. (65.6% yield) of solid LXm. After recrystallization from isopropanol, it melted at 175°–177°C. The IR and NMR were consistent with the structure.

Anal. calc'd. for $C_{17}H_{21}NO_2 \cdot CH_3Br \cdot 1/2H_2O$: C, 57.60; H, 6.71; N, 3.73. Found: C, 57.44; H, 6.78; N, 3.58.

EXAMPLE 39

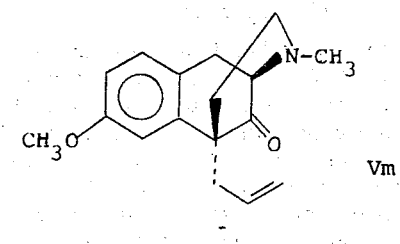

5-Allyl-2'-methoxy-2-methyl-9-oxo-6,7-benzomorphan (Vm).

A suspension of 2 g. (5.46 mmole) LXm in 25 ml. 1-octanol was heated under reflux and nitrogen atmosphere for 15 minutes. After cooling, the mixture was poured into 40 ml. of 0.5N HCl and extracted twice with 100 ml. of petroleum ether to remove octanol. The water layer was basified with aqueous ammonia and the free base extracted with benzene to yield, after drying and evaporation of solvent, 1.23 g. of an oil (VIm). The oil was stirred with a solution of 350 mg. oxalic acid in 5 ml. water for one hour, and it was left at 5° for 16 hours. Separated solid was filtered off to yield 980 mg. (47%) of Vm oxalate, containing one mole of water of crystallization; m.p. 156°–162°C. The product recrystallized from water melted at 160°–161° C. with loss of water at 110° C.

Anal. calc'd. for $C_{17}H_{21}NO_2 \cdot C_2H_2O_4 \cdot H_2O$: C, 60.15; H, 6.64; N, 3.69. Found: C, 60.52; H, 6.72; N, 3.70.

EXAMPLE 40

5-Allyl-9α-Hydroxy-2'-methoxy-2-methyl-6,7-benzomorphan (VIm).

A solution of diisobutylaluminum hydride (62 ml of a 25% solution, ~60 mmol) was diluted with 150 ml of dry tetrahydrofuran and cooled to −45°C under $N_2$. Then a solution of 8.58 g (31.6 mmol) (Vm) in 100 ml of dry tetrahydrofuran was added dropwise. After stirring for 1 hr. at −45°C, 5ml water was carefully added, and the gelatinous material thus obtained was concentrated in vacuo. The residue was extracted with ether, washed with water, dried ($Na_2SO_4$) and evaporated in vacuo to give 8.88 g of the alcohol (VIm). Crystallization of the product from ether-petroleum ether (bp 30°–60°) afforded 6.32 g (72%) of crystalline material (VIm). The mother liquors were purified by chromatography on 100 g of silica gel using a 1:1 mixture of methanol-ether to give 2.00 g (23%) of the pure alcohol (VIm). The analytical sample was recrystallized from acetone-ether-petroleum ether (bp 30°–60°) and melted at 73°–79°C.

Anal. Calc'd. for $C_{17}H_{23}NO_2$: C, 74.69; H, 8.48; N, 5.12. Found: C, 74.26; H, 8.73; N, 5.19.

38

EXAMPLE 41

5-Allyl-9α-hydroxy-2'-methoxy-6,7-benzomorphan (VIIm) hydrogen oxalate.

Substitution in the procedure of example 6 for the compound VIa used therein of an equimolar quantity of compound VIm produced the title compound VIIm. The compound was purified by crystallization of the oxalate salt from methanolether to give a sample melting at 173°–176°C. The analytical sample was purified by molecular distillation of free base at 150°C/5×10⁻⁴ mmHg.

Anal. calc'd. for $C_{16}H_{21}NO_6$: C, 74.10; H, 8.16; N, 5.40. Found: C, 73.92; H, 8.27; N, 5.36.

EXAMPLE 42

5-Allyl-2-cyclopropylmethyl-2',9α-dimethoxy-6,7-benzomorphan (XIm).

A.

5-Allyl-N-cyclopropylcarbonyl-9α-hydroxy-2'-methoxy-6,7-benzomorphan (IXm).

A solution of 4.07 g (15.7 mmol) of the hydroxy amine VIIm in 200 ml of dichloromethane and 5 ml of triethylamine under $N_2$ was treated dropwise with 1.80 g (17.25 mmol) of cyclopropyl carbonyl chloride. The reaction mixture was washed with dilute hydrochloric acid, water, dried ($MgSO_4$) and the solvent removed in vacuo to give 4.12 g (80%) of the crude amide (IXm). Crystallization from benzene-ether afforded a sample melting at 146°–147°C.

Anal. calc'd. for $C_{20}H_{25}NO_3$: C, 73.37; H, 7.70; N, 4.28. Found: C, 73.53; H, 7.71; N, 4.32.

B.

5-Allyl-N-cyclopropylcarbonyl-2',9α-dimethoxy-6,7-benzomorphan (Xm).

To a suspension of 950 mg (21.9 mmol) of a 55% sodium hydride dispersion in mineral oil washed with benzene, in 125 ml of dry dimethylformamide under $N_2$, was added 2.39 g (7.30 mmol) of the alcohol (IXm). The mixture was stirred at 50° C for 0.5 hr., then cooled to room temperature and treated with 5.18 g (36.5 mmol) of methyl iodide. Stirring was maintained for 3.0 hrs. Then the reaction mixture was poured into 500 ml of water and extracted with benzene. The extracts were washed with water, dried ($MgSO_4$) and evaporated in vacuo to give 2.45 g (quantitative) of the amide (Xm). The crude product was purified by an evaporative distillation at 160°C/5×10⁻⁴ mmHg.

Anal. calc'd. for $C_{21}H_{27}NO_3$: C, 73.87; H, 7.97; N, 4.10. Found: C, 74.08; H, 8.11, N, 4.05.

C.

5-Allyl-N-cyclopropylmethyl-2',9α-dimethoxy-6,7-benzomorphan (XIm).

To a suspension of 770 mg (20.2 mmol) of lithium aluminum hydride in 125 ml of dry tetrahydrofuran was added 2.30 g (6.74 mmol) of the amide (IXm). The mixture was refluxed for 3 hours and then cooled and the excess hydride destroyed by adding successively 0.77 ml of water, 0.58 ml of 20% NaOH and finally 2.70 ml of water. The inorganic salts were filtered off and washed with THF. The filtrate was evaporated to dryness and the residual oil taken up in N hydrochloric acid and extracted with ether. The aqueous phase was basified with ammonium hydroxide and extracted with dichloromethane. The extracts were washed with water, dried (MgSO₄) and the solvent removed in vacuo. There was obtained 1.97 g (90%) of the tertiary amine (XIm). Its hydrochloric acid salt melted at 156°–157°C when recrystallized from methanol-ether.

Anal. calc'd. for C₂₁H₂₉NO₂: C, 77.04; H, 8.93; N, 4.28 Found: C, 77.02; H, 9.03; N, 4.30.

EXAMPLE 43

5-Allyl-2-cyclopropylmethyl-2'-hydroxy-9α-methoxy-6,7-benzomorphan (XIIm).

A solution of sodium thioethoxide was prepared by adding 1.70 ml (22.2 mmol) of ethanethiol to 970 mg (22.2 mmol) of a 55% sodium hydride dispersion in mineral oil washed with benzene, in 175 ml of dry dimethylformamide, under N₂. To the reagent thus obtained was added 1.32 g (4.04 mmol) of the dimethyl ether XIm and the solution was refluxed for 4 hours. The reaction mixture was then poured into 500 ml of ice cold water, acidified to pH4 with hydrochloric acid, basified with ammonium hydroxide and extracted with benzene. The extracts were washed with water, dried (MgSO₄) and evaporated in vacuo to give 1.23 g (97%) of the phenol (XIIm). The hydrochloric acid salt was crystallized from methanol-ether and melted at 223°–225°C.

Anal. calc'd. for C₂₀H₂₇NO₂: C, 76.64; H, 8.68; N, 4.47. Found: C, 76.59; H, 8.80; N, 4.39.

EXAMPLE 44

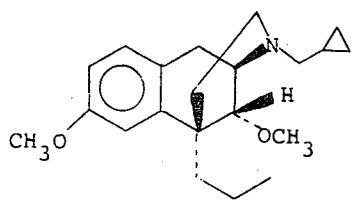

2-Cyclopropylmethyl-2',9α-dimethoxy-5-propyl-6,7-benzomorphan (XIn).

A solution of 0.600 g. (1.87 mmole) of XIm in 20 ml. of absolute ethanol is introduced into a hydrogenation bottle containing 0.100 g. of 10% palladium on charcoal. The resulting mixture is shaken under 60 psi of hydrogen for two hours at room temperature. The catalyst was removed by filtration and the filtrate evaporated to dryness to yield XIn.

EXAMPLE 45

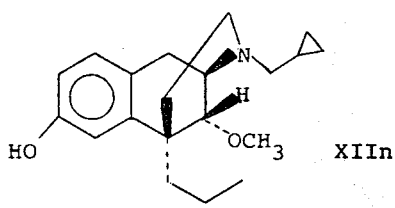

2-cyclopropylmethyl-2'-hydroxy-9α-methoxy-5-propyl-6,7-benzomorphan (XIIn).

Substitution in the procedure of example 8 for the compound XIa used therein of an equimolar quantity of XIn produces the title product identical to that prepared in example 60A.

EXAMPLE 46

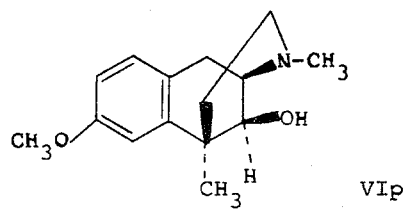

2,5-Dimethyl-9β-hydroxy-2'-methoxy-6,7-benzomorphan hydrobromide (VIp).

A suspension of IVa(0.04 m) in 200 ml ether was treated with 50 ml of a 2.5 m solution of isopropyl magnesium chloride in tetrahydrofuran. This mixture was stirred under nitrogen for 17 hours. The cooled mixture was slowly treated with water (200 ml) and conc. hydrobromic acid (25 ml). The ether was removed by evaporation at reduced pressure. Extraction of the aqueous mixture with methylene chloride gave a tan foam (17 g). This foam was taken up in 95% ethanol (200 ml) and hydrogenated on a Parr shaker using palladium hydroxide on carbon as catalyst to give 10.3 g. (78%) pure VIp after crystallization from 2-propanol.

Reference: H. Kugita and E. L. May, J. Org. Chem., 26, 1954 (1961).

EXAMPLE 47

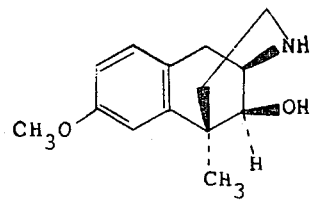

9β-Hydroxy-2'-methoxy-5-methyl-6,7-benzomorphan (VIIp).

A mixture of VIp free base (0.031 m) and 90 ml acetic anhydride was heated at 100° for 1 hour. The acetic anhydride was removed at reduced pressure. Treatment of the residue with sodium carbonate and extraction with methylene chloride afforded a quantitative yield of 2,5-dimethyl-2'-methoxy-9β-acetoxy-6,7-benzomorphan. This material was taken up in benzene (100 ml) and treated with potassium carbonate (5 g) and ethyl chloroformate (10 ml). This mixture was heated at reflux under nitrogen for 26 hours. This mixture was treated with water. The benzene layer was separated and washed with dilute hydrochloric acid and saturated sodium chloride to afford after concentration a quantitative yield of 5-methyl-2'-methoxy-2-carbethoxy-9β-acetoxy-6,7-benzomorphan. This material was taken up in 95% ethanol (250 ml) and treated with 30 g potassium hydroxide. This was heated at reflux under nitrogen for 90 hours. The ethanol was removed at reduced pressure. Treatment of the residue with 10% sodium bicarbonate and extraction with methylene chloride afforded 7.2 g. VIIp (100%). Recrystallization from toluene gave analytically pure material (6.8 g - 94%); mp 132.0°–133.5° C.

EXAMPLE 48

2,5-Dimethyl-9-(spiro-β-epoxy)-2'-methoxy-6,7-benzomorphan (XX).

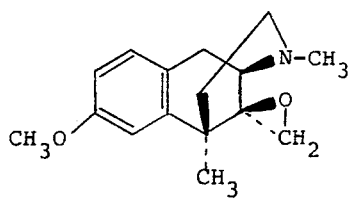

XX

A solution of 2,5-dimethyl-2'-methoxy-9-oxo-6,7-benzomorphan (Va) (0.05 m) in 125 ml dry dimethylsulfoxide was added to a 55% sodium hydride dispersion (0.1 m) with stirring under nitrogen. To this mixture was added trimethylsulfonium iodide (0.1 m) with stirring. After stirring for 4 hours under nitrogen, the mixture was diluted with water and extracted with methylene chloride. Drying and concentration of these extracts gave an oil which GLC analysis indicated to contain 86% β-isomer (XX), 6–7% of another product believed to be α-isomer and some starting ketone. Chromatography on alumina followed by crystallization from cyclohexane gave pure XX (64% yield purity); >95% isomer purity); mp 93°–95°C.

Anal. calc'd. for $C_{16}H_{21}NO_2$: C, 74.10; H, 8.16; N, 5.40. Found: C, 73.89; H, 8.30; N, 5.36.

EXAMPLE 49

9β-Hydroxy-2'-methoxy-2,5,9α-trimethyl-6,7-benzomorphan hydrochloride (VIr).

A solution of 2,5-dimethyl-9-(spiro-β-epoxy)-2'-methoxy-6,7-benzomorphan (XX) (0.028 m) in 75 ml tetrahydrofuran was added to a stirred suspension of lithium aluminum hydride (0.045 m) in 25 ml tetrahydrofuran (THF). This mixture was stirred at 25°C for 16 hours and heated at reflux for 2 hours. This mixture was cautiously treated with 5 ml saturated sodium sulfate. The solids were removed by filtration and the filtrates concentrated to dryness. The residual oil was converted to a hydrochloride and crystallized from ethanol-ethyl acetate-water to give pure VIr hydrochloride hydrate (86% yield); mp 139°–143.0° C. GLC analysis on the free base indicated an isomer purity of 96%. Solution infrared spectra (CCl₄) at different concentrations shows only bonded OH indicating the β-OH configuration.

Reference: E. L. May and H. Kugita, J. Org. Chem., 26 188 (1974).

EXAMPLE 50

Preparation of 9β-Acetoxy-2-carbethoxy-5,9α-dimethyl-2'-methoxy-6,7-benzomorphan (XXI).

9β-Hydroxy-2'-methoxy-2,5,9α-trimethyl-6,7-benzomorphan (VIr) (0.022 m) was treated with 50 ml acetic anhydride and heated on a steam bath for 3 hours. After removal of the acetic anhydride at reduced pressure, the residue was treated with dilute sodium carbonate and extracted with benzene. Drying and evaporation of the benzene extracts yielded the acetoxy compound 9β-acetoxy-2,5,9α-trimethyl-2'-methoxy-6,7-benzomorphan. A solution of this material in benzene was treated with 2.5 g potassium carbonate and 6.5 ml ethyl chloroformate (0.07 m) and heated at reflux for 16 hours. This mixture was cautiously treated with 120 ml 1N hydrochloric acid. The layers were separated and the aqueous layer was extracted with benzene. Drying and concentration of the combined benzene extracts gave title product (XXI) which was recrystallized from 95% ethanol; mp 87.5°–88.5°C.

Anal. calc'd. for $C_{20}H_{27}NO_5$: C, 66.46 H, 7.53; N, 3.88. Found: C, 66.18; H, 7.62; N, 3.75.

EXAMPLE 51

Preparation of 5,9α-Dimethyl-9β-hydroxy-2'-methoxy-6,7-benzomorphan (VIIr).

A mixture of 9β-acetoxy-2-carbethoxy-5,9α-dimethyl-2'-methoxy-6,7-benzomorphan (XXI) (0.002 m), 2.5 g potassium hydroxide and 20 ml 95% ethanol was heated at reflux for 18 hours. After concentration, the residue was treated with water and extracted with methylene chloride to give the title product VIIr which was recrystallized from ethyl acetate; mp 147.0°–148.0°C.

Anal. calc'd. for $C_{15}H_{21}NO_2$: C, 72.84; H, 8.56; N, 5.66. Found: C, 73.12; H, 8.63; N, 5.82.

EXAMPLE 52

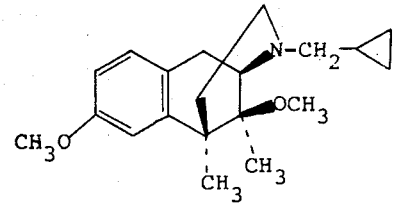

XIr

2-Cyclopropylmethyl-2'-9β-dimethoxy-5,9α-dimethyl-6,7-benzomorphan (XIr).

A solution of 5,9α-dimethyl-9β-hydroxy-2'-methoxy-6,7-benzomorphan (VIIr) (0.005 m) in 25 ml methylene chloride and 7.5 ml triethylamine was treated with cyclopropylcarbonyl chloride (3 ml) with stirring. This mixture was stirred for 18 hours and then treated with dilute sodium carbonate. The layers were separated and the aqueous layer extracted with methylene chloride. Drying and concentration of the methylene chloride extracts gave 2-cyclopropylcarbonyl-5,9α-dimethyl-9β-hydroxy-2'-methoxy-6,7-benzomorphan (IXr) as an oil.

A solution of IXr in dimethylformamide (25 ml) was added to a suspension of NaH (0.015 m) in dimethylformamide (10 ml) under nitrogen. After ½ hour, methyl iodide was added in two portions one hour apart (1 ml each time), and the mixture was stirred an additional 16 hours. After removal of the solvent at reduced pressure, the residue was treated with water and extracted with methylene chloride to give 2-cyclopropylcarbonyl-2',9β-dimethoxy-5,9α-dimethyl-6,7-benzomorphan (Xr). This material was taken up in tetrahydrofuran (30 ml) and added to a stirred suspension of Anal. calc'd. for $C_{14}H_{19}NO_2$: C, 72.07; H, 8.21; N, 6.00. Found: C, 72.08; H, 8.03; N, 6.08.

lithium aluminum hydride (1.0 g) in tetrahydrofuran (20 ml). After an 18 hour reflux period, this mixture was cautiously treated with 3 ml saturated sodium sulfate and warmed until solids were white. Removal of the solids by filtration and concentration of the filtrate gave an oil (XIr) which was converted to its hydrochloride salt; m.p. 226°–229°C.

Anal. calc'd. for $C_{20}H_{29}NO_2 \cdot HCl$: C, 68.26; H, 8.59; N, 3.98. Found: C, 68.16; H, 8.85; N, 4.02.

EXAMPLE 53

2-Cyclopropylmethyl-5,9α-dimethyl-2'-hydroxy-9β-methoxy-6,7-benzomorphan (XIIr).

Substitution in the procedure of example 8 for the compound XIa used therein of an equimolar quantity of compound XIr produced the title compound as the hydrochloride salt; m.p. 270°–278° C. with decomposition.

Anal. calc'd. for $C_{19}H_{27}NO_2 \cdot HCl$: C, 67.54; H, 8.35; N, 4.15. Found: C, 67.32; H, 8.52; N, 4.37.

EXAMPLE 54

2-Cyclobutylmethyl-2',9β-dimethoxy-5-methyl-6,7-benzomorphan (XIs).

Substitution in the procedure of example 52 for the VIIr and cyclopropylcarbonyl chloride used therein of equimolar quantities of VIIp and cyclobutylcarbonyl chloride respectively produced the title compound as the hydrochloride salt; m.p. 205°–209°C.

Anal. calc'd. for $C_{20}H_{29}NO_2 \cdot HCl$: C, 68.26; H, 8.59; N, 3.98. Found: C, 68.58; H, 8.50; N, 4.07.

EXAMPLE 55

2-Cyclobutylmethyl-2'-hydroxy-9β-methoxy-5-methyl-6,7-benzomorphan (XIIs).

Substitution in the procedure of example 8 for the compound XIa used therein of an equimolar quantity of compound XIs produced the title compound as the hydrochloride salt; m.p. 214°–219°C.

Anal. calc'd. for $C_{19}H_{27}NO_2 \cdot HCl$: C, 67.54; H, 8.35; N, 4.15. Found: C, 67.88; H, 8.41; N, 4.02.

EXAMPLE 56

2-Cyclopropylmethyl-2',9β-dimethoxy-5-methyl-6,7-benzomorphan (XIt).

Substitution in the procedure of example 52 for the VIIr used therein of an equimolar quantity of VIIp produced the title compound as the hydrochloride salt; m.p. 217°–220°C.

Anal. calc'd. for $C_{19}H_{27}NO_2 \cdot HCl$: C, 67.54; H, 8.35; N, 4.15. Found: C, 67.53; H, 8.65; N, 3.86.

EXAMPLE 57

2-Cyclopropylmethyl-2'-hydroxy-9β-methoxy-5-methyl-6,7-benzomorphan (XIIt).

Substitution in the procedure of example 8 for the compound XIa used therein of an equimolar quantity of compound XIt produced the title compound as the hydrochloride salt; m.p. 245°–255°C. with decomposition.

Anal. calc'd. for $C_{18}H_{25}NO_2 \cdot HCl$: C, 66.75; H, 8.09; N, 4.33. Found: C, 67.11; H, 8.28; N, 4.17

EXAMPLE 58

2-Cyclobutylmethyl-2',9β-dimethoxy-5,9α-dimethyl-6,7-benzomorphan (XIv).

Substitution in the procedure of example 52 for the cyclopropylcarbonyl chloride used therein of an equimolar quantity of cyclobutylcarbonyl chloride produced the title compound as an oil which was usable as such in example 59.

EXAMPLE 59

2-Cyclobutylmethyl-5,9β-dimethyl-2'-hydroxy-9β-methoxy-6,7-benzomorphan (XIIv).

Substitution in the procedure of example 8 for the compound XIa used therein of an equimolar quantity of compound XIv produced the title compound as the hydrochloride salt; m.p. >245° C. with decomposition.

Anal. calc'd. for $C_{20}H_{29}NO_2 \cdot HCl$: C, 68.26; H, 8.59; N, 3.98. Found: C, 68.07; H, 8.88; N, 4.02.

EXAMPLE 60A

N-Cyclopropylmethyl-2'-hydroxy-9α-methoxy-5-propyl-6,7-benzomorphan (XIIn).

A solution of 495 mg (1.51 mmol) of the olefin (XIIm) in 150 ml of absolute ethanol was hydrogenated for 1 hour over 250 mg of 10% Pd/C at an initial pressure of 42 psi. The catalyst was filtered over celite and the solvent was evaporated to give 486 mg (98%) of the saturated compound XIIn. The hydrochloric acid salt was crystallized from methanolether and melted at 236°–239°C. The analytical sample was purified by sublimation at $160°C/5\times10^{-4}$ mmHg.

Anal. calc'd. for $C_{20}H_{29}NO_2$: C, 76.15; H, 9.27; N, 4.44. Found: C, 76.17; H, 9.08; N, 4.41.

EXAMPLE 60B

2-Carbethoxy-9α-hydroxy-2'-methoxy-5-methyl-6,7-benzomorphan (XXII).

A solution of VIa (0.015 mole) is dissolved in benzene (75 ml), treated with potassium carbonate (2 g) and ethyl chloroformate (5 ml) and heated at reflux for 18 hours. The resultant mixture is washed with water, dilute hydrochloric acid and saturated sodium chloride. The aqueous layers are extractd twice more with benzene. The benzene layers were dried ($K_2CO_3$) and concentrated to give 9α-Hydroxy-2'-methoxy-2-carbethoxy-5-methyl-6,7-benzomorphan which is used as such in example 61.

EXAMPLE 61

2-Carbethoxy-2',9α-dimethoxy-5-methyl-6,7-benzomorphan (XXIII).

A solution of XXII (0.014 moles) in dimethylformamide (25 ml) is added to a suspension of NaH (0.015 m) in DMF (10 ml) under nitrogen. After ½ hour, methyl iodide is added in 2 portions one hour apart (1 ml each time) and the mixture is stirred an additional 16 hours. The solvent is removed in vacuo, the residue treated with water and extracted with methylene chloride to produce XXIII. The product is isolated by evaporation in vacuo and is usable as such in example 62.

EXAMPLE 62

2',9α-Dimethoxy-5-methyl-6,7-benzomorphan (XXIV).

Compound XXIII (0.014 moles) is hydrolyzed with potassium hydroxide (25-g—85% pellets) in refluxing 95% ethanol (125 ml) for 66 hours. The ethanol is removed at reduced pressure. The residue is treated with dilute sodium bicarbonate and extracted with methylene chloride to give the product XXIV which is collected by evaporation in vacuo. The residue is used as such in example 63.

EXAMPLE 63A

2-Allyl-2',9α-dimethoxy-5-methyl-6,7-benzomorphan (XIw).

A mixture of 0.500 g. (1.8 mmole) of XXIv, 0.300 g. of sodium bicarbonate and 1.8 mmole of allyl bromide in 5 ml. of dry dimethylformamide (DMF) is stirred overnight at room temperature. The reaction mixture is then diluted with ether and filtered. The filtrate is extracted with 0.05N HCl, the layers separated and the acidic layer made alkaline with concentrated ammonium hydroxide before extraction with ether. After drying over potassium carbonate, there is obtained a colorless oil which is the desired product.

EXAMPLE 63B

2-Allyl-2'-hydroxy-9α-methoxy-5-methyl-6,7-benzo-morphan (XIIw).

A solution of 0.420 g. (1.35 mmole) of XIw in 10 ml. of methylene chloride is added slowly to a solution of 1.4 mmole (0.350 g.) of BBr$_3$ in 10 ml. of methylene chloride maintained at −10° C. The resulting mixture is stirred overnight at room temperature. After the usual work up, there is obtained an oil which crystallized from water-methanol and which is the title product.

EXAMPLE 64

(−)-2'-acetoxy-2-Cyclopropylmethyl-9α-methoxy-5-methyl-6,7-benzomorphan.

(−)-XIIa free base (0.001 mole) is dissolved in 1 ml of acetic anhydride and 0.08 ml of pyridine and refluxed for one hour. The solvents are evaporated in vacuo, the residue dissolved in ether and the ether solution washed with dilute ammonium hydroxide solution. The ether layer is dried over sodium sulfate, filtered and evaporated in vacuo to dryness to yield the title product.

EXAMPLE 65

(−)-2-Cyclopropylmethyl-2'-hydroxy-9α-methoxy-5-methyl-6,7-benzomorphan 2'-(4-nicotinoate).

To a solution of 0.002 mole of compound (−) XIIa free base in 3 ml of pyridine is added 0.002 mole of 4-nicotinoyl chloride hydrochloride. The mixture is refluxed for one hour and the solvents evaporated. The residue is partitioned between ether and dilute ammonium hydroxide, the ether layer separated, washed with water, dried over anhydrous sodium sulfate, filtered and evaporated in vacuo to produce the desired title nicotinoyl ester.

EXAMPLE 66

(−)-2-Cyclopropylmethyl-2'-hydroxy-9α-methoxy-5-methyl-6,7-benzomorphan 2'-(3-nicotinoate).

Substitution in the procedure of Example 65 for the 4-nicotinoyl chloride hydrochloride used therein of an equimolar quantity of 3-nicotinoyl chloride produces the desired title product.

EXAMPLE 67

2'-Monomethyl ether of (−)-2-cyclopropylmethyl-2'-hydroxy-9α-methoxy-5-methyl-6,7-benzomorphan.

Chloromethylmethylether (0.01 mole) is placed into 10 ml of dry dimethylformamide and the resulting solution is added to 0.0075 mole of compound (−) XIIa free base dissolved in 20 ml of dry dimethylformamide. Anhydrous sodium carbonate (0.011 mole) as a fine powder is added to the solution with stirring at about room temperature. Stirring is continued for about five hours. The solution is filtered from the sodium carbonate, evaporated to dryness in vacuo to produce the essentially pure title product.

General procedure for the preparation of Fumarate salts

A 1:1 equimolar quantity of fumaric acid powder and the appropriate amine (e.g., XIIb) are dissolved in a sufficient amount of hot isopropanol or n-propanol to achieve solution. Upon cooling, and with scratching or seeding, the fumarate salt crystallizes. The product is collected by filtration.

General procedure for the preparation of oxalate salts

Compound IIIa (0.01 mole) is dissolved in a minimum quantity of hot acetone. A hot solution of oxalic acid (0.01 mole) is added with stirring, scratching and/or seeding. The oxalate salt crystallizes upon cooling and is collected by filtration.

EXAMPLE 68

Resolution of 5-allyl-2-cyclopropylmethyl-2'-hydroxy-9α-methoxy-6,7-benzomorphan into its levo and dextrorotatory isomers.

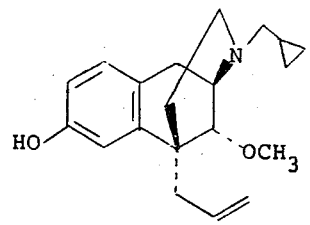

A solution of 5.3 g (16.9 mmol) of the title compound (XIIm) in 150 ml of acetone was treated with 2.6 g (17.0 mmol) of *l*-mandelic acid. The partially resolved solid which came out (2.0 g) was recrystallized three times from acetone to finally give a salt (0.69g) which had rotation $[\alpha]_D^{25}$: +8.4°; conc. 286 mg/100 ml MeOH. The rotation of the free base was $[\alpha]_D^{25}$: +61.0°; conc. 189 mg/100 ml MeOH and the one of its hydrochloric acid salt (m.p. 222°–24°C) was $[\alpha]_D^{25}$: +58.9°; conc. 229 mg/100 ml MeOH.

The *l*-isomer was resolved by dissolving 5.3 g (16.9 mmol) of the title compound in 125 ml of acetone and treating the solution with 2.6 g (17.0 mmol) of d-mandelic acid. The salt which came out (2.86 g) was recrystallized once from acetone to give rotation $[\alpha]_D^{25}$: −9.4°; conc. 287 mg/100 ml MeOH. The free base was generated $[\alpha]_D^{25}$: −62.0°; conc. 266 mg/100 ml MeOH) and then crystallized from acetone-ether as its hydrochloric acid salt (1.3 g, m.p. 222°–24° C). $[\alpha]_D^{25}$: −59.4°; conc. 281 mg/100 ml MeOH.

When the d or l-XIIm was hydrogenated to d or l-XIIn, then the measured rotation of the d-isomer was $[\alpha]_D^{25}$: +52.8°; conc. 303 mg/100 ml MeOH; m.p. 228°–30°C (HCl salt) and the rotation of the l-isomer was $[\alpha]_D^{25}$: −52.7°; conc. 294 mg/100 ml MeOH; m.p. 228°C (HCl salt).

EXAMPLE 69

5-Allyl-2-cyclobutylcarbonyl-9α-hydroxy-2'-methoxy-6,7-benzomorphan (IXz).

A solution of 9.20 g (35.5 mmol) of the hydroxy amine VIIm free base in 400 ml of dichloromethane and 15 ml of triethylamine was treated dropwise at 0°C. and under nitrogen with a solution of 4.62 g (39.0 mmol) of cyclobutylcarbonyl chloride in 100 ml of dichloromethane. The cooling bath was removed after completion of the addition and the solution stirred at room temperature for 1 hr. Then the reaction mixture was washed with 1N hydrochloric acid, water and dried over magnesium sulfate. Evaporation of the solvent in vacuo left 11.40g (94%) of the hydroxy amide (IXz).

Crystallization from ether-petroleum-ether (b.p. 30°–60° C) afforded an analytical sample melting at 116°–118° C.

Anal. calc'd. for $C_{21}H_{27}NO_3$: C, 73.87; H, 7.97; N, 4.10. Found: C, 74.08; H, 8.11; N, 4.01

EXAMPLE 70

5-Allyl-2-cyclobutylcarbonyl-2',9α-dimethoxy-6,7-benzomorphan (Xz).

To a suspension of 1.92 g (43.9 mmol) of NaH (55% in oil, washed with benzene) in 500 ml of dimethylformamide was added 5.0 g (14.6 mmol) of the hydroxy amide IXz. The mixture was heated at 50° C. for 0.5 hrs., then cooled to room temperature and treated with 10.4 g (73.0 mmol) of methyl iodide. After stirring for 3 hrs., the reaction mixture was poured into water and extracted with benzene. The extracts were washed with water, dried ($MgSO_4$) and concentrated in vacuo to give 5.0 g (96%) of the dimethoxy amide (Xz) as a viscous oil. An analytical sample was prepared by evaporative distillation at 170°C/5×10⁻⁴mmHg.

Anal. calc'd. for $C_{22}H_{29}NO_3$: C, 74.33; H, 8.22; N, 3.94. Found: C, 74.08; H, 8.39; N, 3.89.

EXAMPLE 71

5-Allyl-2-cyclobutylmethyl-2',9α-dimethoxy-6,7-benzomorphan (XIz).

A solution of 4.28 g (12.0 mmol) of the dimethoxy amide Xz in 50 ml of tetrahydrofuran was added to a solution of 1.38 g (36.0 mmol) of lithium aluminum hydride in 300 ml of tetrahydrofuran. The reaction mixture was refluxed for 1 hr., cooled and the excess hydride was destroyed by adding successively 1.38 ml of water, 1.02 ml of 20% sodium hydroxide and finally 4.80 ml of water. The inorganic salts were filtered off, washed with tetrahydrofuran and the filtrate evaporated to dryness. The residual oil was taken up in dilute hydrochloric acid and extracted with ether. The aqueous phase was basified with conc. ammonium hydroxide and extracted with dichloromethane. The extracts were washed with water, dried ($MgSO_4$) and evaporated in vacuo to yield 3.80 g (92.7%) of the amine XIz. The oxalic acid salt melted at 184°–186° C after crystallization from methanol-ether.

Evaporative distillation of the free base at 135°C/5×10⁻⁴ mmHg afforded an analytical sample.

Anal. calc'd. for $C_{22}H_{31}NO_2$: C, 77.38; H, 9.15; N, 4.10. Found: C, 77.50; H, 9.32; N, 4.08.

EXAMPLE 72

5-Allyl-2-cyclobutylmethyl-2'-hydroxy-9α-methoxy-6,7-benzomorphan (XIIz).

A solution of sodium ethanethiolate was prepared by adding 1.87 ml (25.5 mmol) of ethanethiol to a suspension of 1.07 g (25.5 mmol) of 55% sodium hydride (suspension in mineral oil; washed with benzene) in 200 ml of dimethylformamide. To this reagent was added 1.52 g (4.6 mmol) of the dimethoxy amine XIz and the solution was refluxed for 5 hrs. Then the reaction mixture was poured into water, made acidic with conc. hydrochloric acid, basified with ammonium hydroxide and extracted with benzene. The extracts were washed with water, dried ($MgSO_4$) and evaporated to dryness. The crude material was dissolved in acetone, treated with one equivalent of oxalic acid and ether was added until crystallization occurs. The oxalic acid salt weighed 1.62 g (83%) and melted at 193°–94° C after crystallization from methanol-ether.

An analytical sample was prepared by evaporative distillation of the free base at 160°–5°C/5×10⁻⁴ mmHg.

Anal. calc'd. for $C_{21}H_{29}NO_2$: C, 77.02; H, 8.93; N, 4.28. Found: C, 77.31; H, 9.04; N, 4.18.

EXAMPLE 73

2-Cyclobutylmethyl-2'-hydroxy-9α-methoxy-5-propyl-6,7-benzomorphan (XIIy).

The olefin XIIz (1.04 g; 3.18 mmol) was dissolved in 200 ml of absolute ethanol and hydrogenated for 2 hrs. over 10% Pd/C at an initial pressure of 47 p.s.i. Then the catalyst was filtered over celite and the filtrate evaporated to dryness. The crude material (922 mg; 88%) was dissolved in acetone, treated with one equivalent of oxalic acid and ether added until cyrstallization starts. The salt thus obtained (1.04 g) melted at 214°–16°C after crystallization from methanol-ether.

An analytical sample was prepared by sublimation of the free base at 160°C/5×10⁻⁴ mmHg. m.p. 181°–83°C.

Anal. calc'd. for $C_{21}H_{31}NO_2$: C, 76.55; H, 9.48; N, 4.25. Found: C, 76.65; H, 9.76; N, 4.25.

EXAMPLE 74

2-Cyclobutylmethyl-2',9α-dimethoxy-5-methyl-6,7-benzomorphan hydrochloride (XIx).

Substitution in the procedure of example 7 for the cyclopropylcarbonyl chloride used therein of an equimolar quantity of cyclobutylcarbonyl chloride produced the title compound XIx; m.p. 181°–184° C.

Anal. calc'd. for $C_{20}H_{29}NO_2 \cdot HCl$: C, 68.26; H, 8.59; N, 3.98. Found: C, 67.99; H, 8.52; N, 3.76.

EXAMPLE 75

2-Cyclobutylmethyl-2'-hydroxy-9α-methoxy-5-methyl-6,7-benzomorphan fumarate (XIIx).

Substitution in the procedure of example 8 for the compound XIa used therein of an equimolar quantity of XIx produced the title compound XIIx free base. It was isolated as the fumarate salt, m.p. 163.5°–165.5° C.

Anal. calc'd. for $C_{19}H_{27}NO_2 \cdot \frac{1}{2}(C_4H_4O_4)$: C, 70.17; H, 8.13; N, 3.90. Found: C, 70.01; H, 8.04; N, 3.62.

EXAMPLE 76

General procedure for the preparation of tartaric acid salts

A 1:1 equimolar quantity of d- or l- or dl-tartaric acid and the appropriate amine (e.g. XIIa) are dissolved in a sufficient amount of hot isopropanol or n-propanol to achieve solution. Upon cooling, and with scratching or seeding, the tartrate salt crystallizes. The product is collected by filtration.

EXAMPLE 77

Preparation of
(−)-2-Cyclopropylmethyl-2′-hydroxy-9α-methoxy-5-methyl-6,7-benzomorphan d-tartrate salt.
[(−)-XIIa-d-tartrate].

Substitution in the procedure of example 76 for the appropriate amine XIIa, used therein of (−)-XIIa, (−)-2-cyclopropylmethyl-2′-hydroxy-9α-methoxy-5-methyl-6,7-benzomorphan produced the title d-tartrate salt [(−)-XIIa-d-tartrate]; m.p. 146.5°–148.5°C.

$[\alpha]_D^{20}$ −37.5° (c, 0.986), 95% ethanol).

Anal. calc'd. for $(C_{18}H_{25}NO_2)_2C_4H_6O_6 \cdot \frac{1}{2}H_2O$: C, 64.67; H, 7.87; N, 3.77; $H_2O$, 2.42. Found: C, 64.34; H, 7.51; N, 3.86; $H_2O$, 3.25.

EXAMPLE 78

5-Allyl-2,9β-dimethyl-9α-hydroxy-2′-methoxy-6,7-benzomorphan (VIu).

A solution of 113.5 g (0.80 mmol) of methyliodide in 100 ml of anhydrous ether was added dropwise to 19.4 g (0.80 mmol) of magnesium covered with 400 ml of anhydrous ether in a 3-1 three-necked flask. When the reaction with magnesium was completed, the mixture was warmed to 60°C. in an oil-bath, the solvent evaporated under a flow of nitrogen and the residual material submitted to vacuum (0.5 mmHg/60° C) for 1 hr. The flask, kept under nitrogen, was equipped with a mechanical stirrer and a dropping funnel. Then a solution of 57.4 g (0.20 mmol) of ketone Vm in 1.0 1 l petroleum ether (30°–60°C) was added over a 15 min. period with vigorous stirring. After stirring at 20°–25°C for 18 hrs., 400 ml of water was carefully added and the heavy slurry thus obtained was treated with conc. hydrochloric acid and the pH adjusted to 8. The organic layer was separated and the aqueous phase extracted twice with 600 ml of ether. The organic extracts were dried ($Na_2SO_4$) and evaporated in vacuo leaving 57.5 g (100%) of VIu as an oil containing a trace of the β-OH isomer. Crystallization of the oxalic acid salt from methanol-ether afforded an analytical sample melting at 208°–209° C.

Anal. calc'd. for $C_{18}H_{25}NO_2 \cdot C_2H_2O_4$: C, 63.65; H, 7.21; N, 3.71. Found: C, 63.78; H, 7.41; N, 3.92.

EXAMPLE 79

5-Allyl-2-cyano-9α-hydroxy-2′-methoxy-9β-methyl-6,7-benzomorphan (XXVu).

A solution of 0.60 g (5.75 mmol) of cyanogen bromide in 25 ml of chloroform was added dropwise to a solution of 1.52 g (5.26 mmol) of VIu in 25 ml of chloroform. After refluxing for 22 hrs., the solvent was evaporated under vacuum leaving 1.69 g of a brown oil which was dry chromatographed over silica gel. Elution with ether afforded 1.32 g (83.5%) of XXVu. An analytical sample (m.p. 103°–5°) was obtained from ether-petroleum ether.

Anal. calc'd. for $C_{18}H_{22}N_2O_2$: C, 72.45; H, 7.43; N, 9.39. Found: C, 72.56; H, 7.48; N, 9.23.

EXAMPLE 80

5-Allyl-9α-hydroxy-2′-methoxy-9β-methyl-6,7-benzomorphan (VIIu).

To a suspension of 0.20 g (5.3 mmol) of lithium aluminum hydride in 25 ml of dry tetrahydrofuran cooled in an ice bath was added dropwise a solution of 0.75 g (2.5 mmol) of XXVu in 30 ml of tetrahydrofuran. After 17 hrs. of reflux, the reaction mixture was cooled in an ice bath, and the excess of hydride was destroyed with 0.2 ml of water, 0.15 ml of a 20% sodium hydroxide solution and 0.70 ml of water. The solid material thus obtained was filtered off and the filtrate was evaporated to dryness leaving 0.58 g (85%) of an oil (VIIu), which was N-acylated without purification in example 81.

EXAMPLE 81

5-Allyl-2-cyclopropylcarbonyl-9α-hydroxy-2′-methoxy-9β-methyl-6,7-benzomorphan (IXu).

A solution of 0.31 g (3.0 mmol) cyclopropylcarboxylic acid chloride in 5 ml of methylene chloride was added to a solution of 0.75 (2.7 mmol) of VIIu in 20 ml of methylene chloride and 0.4 ml of triethylamine cooled in an ice bath. The cold bath was removed, the reaction mixture left at 20° for 30 mins. and the solid filtered off and washed with ether. The residual filtrate was washed with dilute ammonium hydroxide and water, dried ($Na_2SO_4$) and evaporated under vacuum leaving 1.00 g of an oil which was crystallized from ligroin; 0.79 g (84%).

Anal. calc'd. for $C_{21}H_{27}NO_3$: C, 73.87; H, 7.97; N, 4.10 Found: C, 73.80; H, 8.00; N, 4.01.

EXAMPLE 82

5-Allyl-2-cyclopropylcarbonyl-2′,9α-dimethoxy-9β-methyl-6,7benzomorphan (Xu).

To a suspension of 130 mg (3 mmol) of sodium hydride (55% in mineral oil; washed with benzene) in 10 ml of dimethylformamide was added a solution of 341 mg (1 mmol) of the alcohol IXu in 10 ml of dimethylformamide. The mixture was stirred at 70°C for 0.5 hrs., then cooled to room temperature and treated with 710 mg (5 mmol) of methyliodide in 10 ml of dimethylformamide. After stirring for 3 hrs., the reaction mixture was poured into water and extracted with benzene. The organic extracts were dried ($MgSO_4$) and evaporated to dryness leaving 350 mg (99%) of Xu as a colorless oil.

An evaporative distillation at 150°–55°C/3×10$^{-2}$ mmHg gave an analytical sample.

Anal. calc'd. for $C_{22}H_{29}NO_3$: C, 74.33; H, 8.22, N, 3.94. Found: C, 74.14; H, 8.40; N, 3.87.

EXAMPLE 83

5-Allyl-2-cyclopropylmethyl-2′,9α-dimethoxy-9β-methyl-6,7-benzomorphan (XIu).

A solution of 711 mg (2 mmol) of the amide Xu in 15 ml of tetrahydrofuran was added to a suspension of 228 mg (6 mmol) of lithium aluminum hydride in 35 ml of tetrahydrofuran. The mixture was refluxed under nitrogen for 45 mins., then cooled to room temperature and the excess hydride destroyed by adding 0.23 ml of water, 0.17 ml of 20% sodium hydroxide and finally 0.81 ml of water. The inorganic salts were filtered off, washed with tetrahydrofuran and the filtrate evaporated to dryness. The residue was taken up in 1N hydrochloric acid, extracted with ether, basified with ammonium hydroxide and extracted with dichloromethane. The extracts were washed with water, dried ($MgSO_4$) and evaporation of the solvent left 570 mg (83.5% of the amine XIu as an oil. Evaporation distillation at 145°C/5×10$^{-3}$ mmHg gave an analytical sample.

Anal. calc'd. for $C_{22}H_{31}NO_2$: C, 77.38; H, 9.15; N, 4.10. Found: C, 77.19; H, 9.23; N, 4.06.

EXAMPLE 84

5-Allyl-2-cyclopropylmethyl-2'-hydroxy-9α-methoxy-9β-methyl-6,7-benzomorphan (XIIu).

A solution of sodium ethanethiolate was prepared by adding 2.2 ml (29 mmol) of ethanethiol to a suspension of 1.27 g (29 mmol) of sodium hydride (55% mineral oil; washed with benzene) in 150 ml of dimethylformamide. To that reagent was added a solution of 1.8 g (5.27 mmol) of the amine XIu in 25 ml of dimethylformamide and the mixture was refluxed under nitrogen for 6 hrs. Then the reaction mixture was poured into water, acidified to pH~3 with conc. hydrochloric acid, basified with conc. ammonium hydroxide and extracted with benzene. The extracts were washed with brine, dried over $MgSO_4$ and evaporated to dryness. The oil thus obtained was dissolved in ether, treated with ethereal hydrogen chloride and the salt which precipitated out was recrystallized from methanolether to yield XIIu hydrochloride.

Yield: 1.32 g (70%), m.p. 248° – 50°C. Evaporative distillation of the free base (145° – 50°C/5×10$^{-3}$mmHg) afforded an analytical sample. Anal. calc'd. for $C_{21}H_{29}NO_2$: C, 77.02; H, 8.93; N, 4.28. Found: C, 76.76; H, 9.10; N, 4.38.

EXAMPLE 85

2-Cyclopropylmethyl-2'-hydroxy-9α-methoxy-9β-methyl-5-propyl-6,7-benzomorphan (XIIuu).

A solution of 800 mg (2.38 mmol) of the olefin XIIu in 150 ml of absolute ethanol was hydrogenated for 1.5 hrs. over 250 mg of 10% Pd/C at an initial pressure of 52 p.s.i. Then the catalyst was filtered off and the solvent removed in vacuo leaving 670 mg (84%) of XIIuu. The saturated compound was purified by crystallization of its hydrochloric acid salt from methanol-ether, m.p. 238°–240°C.

Distillation (145°C/2×10$^{-3}$mmHg) of the free base gave an analytical sample. Anal. calc'd. for $C_{21}H_{31}NO_2$: C, 76.55; H, 9.48; N, 4.25. Found: C, 76.36: H, 9.55; N, 4.20.

EXAMPLE 86

5-Allyl-2-cyclobutylcarbonyl-9α-hydroxy-2'-methoxy-9β-methyl-6,7-benzomorphan (IXq).

A solution of 720 mg (2.63 mmol) of the hydroxy amine VIIu in 25 ml of dichloromethane and 2 ml of triethylamine was cooled to 0°C and treated dropwise with 343 mg (2.90 mmol) of cyclobutylcarboxylic acid chloride in 10 ml of dichloromethane. The cooling bath was removed and the solution stirred at room temperature for 1 hr. Then the reaction mixture was washed with 1N HCl, water, dried ($MgSO_4$) and evaporated to dryness. There was obtained 810 mg (86.6%) of the amide IXq which was crystallized from ether-pet.-ether (30°–60°C), m.p. 112°–113°C.

Anal. calc'd. for $C_{22}H_{29}NO_3$: C, 74.33; H, 8.22; N, 3.94. Found: C, 74.25; H, 8.47; N, 3.83.

EXAMPLE 87

5-Allyl-2-cyclobutylcarbonyl-2'-9α-dimethoxy-9β-methyl-6,7-benzomorphan (Xq).

To a suspension of 262 mg (6 mmol) of sodium hydride (55% in mineral oil; washed with benzene) in 50 ml of dimethylformamide was added 711 mg (2 mmol) of the hydroxy amide IXq and the mixture was stirred at 85°C for 0.5 hrs. Then the reaction mixture was cooled to room temperature and treated with 1.42 g (10 mmol) of methyliodide. After stirring for 1 hr., the solution was diluted with water and extracted with benzene. The extracts were washed with water, dried ($MgSO_4$) and the solvent removed in vacuo. The dimethoxy amide Xq was obtained as a viscous oil in quantitative yield.

Anal. calc'd. for $C_{23}H_{31}NO_3$: C, 74.76; H, 8.46; N, 3.79. Found: C, 74.50; H, 8.87; N, 3.72.

EXAMPLE 88

5-Allyl-2-cyclobutylmethyl-2'-9α-dimethoxy-9β-methyl-6,7-benzomorphan (XIq).

A solution of 740 mg (2 mmol) of the amide Xq in 50 ml of tetrahydrofuran was added to a suspension of 380 mg (10 mmol) of lithium aluminum hydride in 50 ml of tetrahydrofuran. The reaction mixture was refluxed for 1.5 hrs., then cooled and the excess hydride destroyed by adding 0.38 ml of water, 0.29 ml of 20% sodium hydroxide and finally 1.33 ml of water. The inorganic salts were filtered, washed with tetrahydrofuran and the filtrate evaporated to dryness. The residual oil was taken up in 1N hydrochloric acid, extracted with ether, basified with conc. ammonium hydroxide and extracted with dichloromethane. The organic extracts were washed with water, dried ($MgSO_4$) and evaporated to give 470 mg (66%) of XIq as an oil. The hydrochloric acid salt melted at 206° – 209°C after recrystallization from methanolether.

Anal. calc'd. for $C_{23}H_{33}NO_2$.HCl: C, 70.48; H, 8.74; N, 3.57. Found: C, 70.42; H, 9.00; N, 3.44

EXAMPLE 89

5-Allyl-2-cyclobutylmethyl-2'-hydroxy-9α-methoxy-9β-methyl-6,7-benzomorphan (XIIq).

A solution of sodium ethanethiolate was prepared by adding 0.84 ml (11 mmol) of ethanethiol to a suspension of 480 mg (11 mmol) of sodium hydride (55% in mineral oil; washed with benzene) in 50 ml of dimethylformamide. To that reagent was added 711 mg (2 mmol) of the dimethoxy amine XIq dissolved in 25 ml of dimethylformamide and the reaction mixture was refluxed under nitrogen for 4 hrs. Then the solution was poured into 350 ml of water, acidified to pH 4 with conc. hydrochloric acid, basified with conc. ammonium hydroxide and finally extracted with benzene. The extracts were washed with water, dried ($MgSO_4$) and evaporated to dryness. The residual oil was taken up in ether and treated with ethereal hydrogen chloride. The precipitated salt was crystallized from methanol-ether. Yield: 400 mg (53%), m.p. 222°–24°C (XIIq).

The free base was distilled evaporatively (150°C/5×10⁻⁴mmHg) to give an analytical sample.

Anal. calc'd. for $C_{22}H_{31}NO_2$: C, 77.38; H, 9.15; N, 4.10. Found: C, 77.45; H, 9.41; N, 4.05.

EXAMPLE 90

2-Cyclobutylmethyl-2'-hydroxy-9α-methoxy-9β-methyl-5-propyl-6,7-benzomorphan (XIIqq).

solution of 900 mg (2.6 mmol) of the olefin XIIq in 300 ml of absolute ethanol was hydrogenated over 300 mg of 10% Pd/C for 1.5 hrs. at an initial pressure of 51.5 p.s.i. Then the catalyst was filtered off and evaporation of the filtrate left 870 mg (96.5%) of XIIqq as a thick oil. The compound was purified by crystallization of its hydrochloric acid salt. M.P. 226°–28°C. The free base was distilled at 150°C/5×10⁻⁴ mmHg to give an analytical sample.

Anal. calc'd. for $C_{22}H_{33}NO_2$: C, 76.92; H, 9.68; N, 4.08. Found: C, 76.74; H, 9.84; N, 4.05.

We claim:
1. A compound having the formula

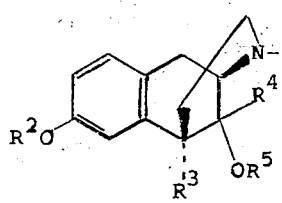

wherein $R^1$ is selected from the group consisting of H, $-CH_2-C\equiv CH$, $-CH_2-CH=CH_2$,

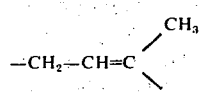

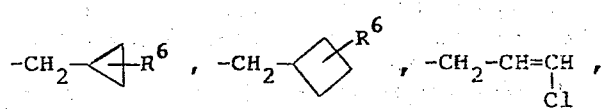

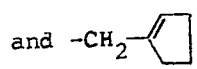

in which $R^6$ is H or $CH_3$; $R^2$ is selected from the group consisting of H, (lower)alkyl, (lower)alkanoyl,

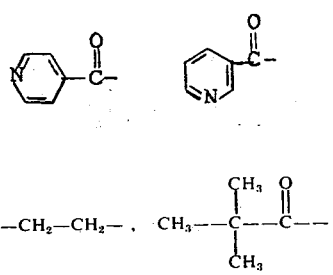

$CH_3O-CH_2-$ ,

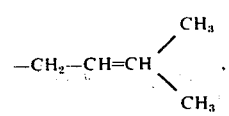

$R^5$ is selected from the group consisting of (lower)alkyl, allyl and propargyl, $R^4$ is H or (lower)alkyl and $R^3$ is (lower)alkyl or (lower)alkenyl; or a pharmaceutically acceptable acid addition salt thereof.

2. A compound having the formula

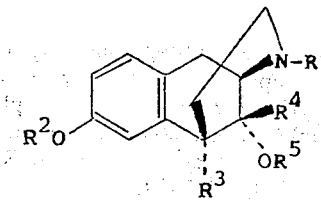

wherein $R^1$ is selected from the group consisting of H, $-CH_2-C\equiv CH$, $-CH_2-CH=CH_2$,

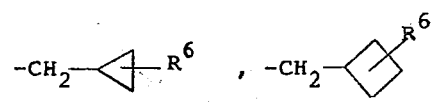

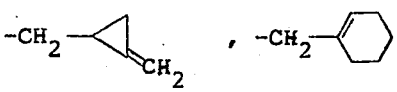

and $-CH_2-$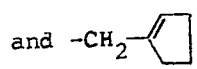

in which $R^6$ is H or $CH_3$; $R^2$ is selected from the group consisting of H, (lower)alkyl, (lower)alkanoyl,

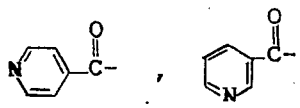

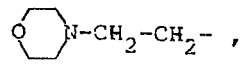

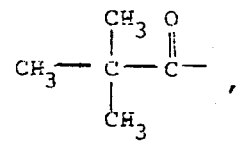

$CH_3O-CH_2-$ ,

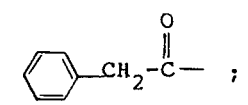

$R^5$ is selected from the group consisting of (lower)alkyl, allyl and propargyl, $R^4$ is H or (lower)alkyl and $R^3$ is (lower)alkyl or (lower)alkenyl; or a pharmaceutically acceptable acid addition salt thereof.

3. A compound of claim 2 wherein $R^1$ is $-CH_2-C \equiv CH$, $-CH_2-CH=CH_2$,

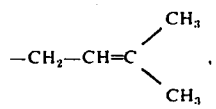

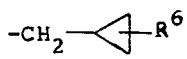

or

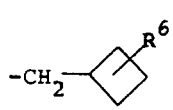

in which $R^6$ is H or $CH_3$, $R^2$ is H, $CH_3$,

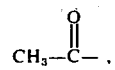

or

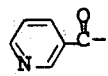

and $R^5$ is $CH_3$, $C_2H_5$, propyl, allyl or propargyl, $R^4$ is H and $R^3$ is $CH_3$, ethyl, propyl or allyl; or a pharmaceutically acceptable acid addition salt thereof.

4. A compound of claim 2 wherein $R^1$ is $-CH_2-CH=CH_2$,

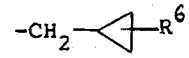

or

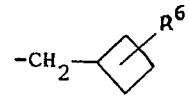

in which $R^6$ is H or $CH_3$, $R^2$ is H, $CH_3$,

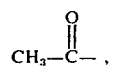

or

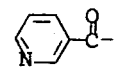

and $R^5$ is $CH_3$, $C_2H_5$, propyl, allyl or propargyl, $R^4$ is H and $R^3$ is $CH_3$ or a pharmaceutically acceptable acid addition salt thereof.

5. A compound of claim 2 wherein $R^1$ is

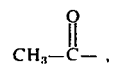

or $-CH_2-CH=CH_2$, $R^2$ is H, $CH_3$ or $CH_3-\overset{O}{\overset{\|}{C}}-$ , $R^5$ is methyl, $R^4$ is H and $R^3$ is methyl; or a pharmaceutically acceptable acid addition salt thereof.

6. (—)-2-Cyclopropylmethyl-2'-hydroxy-9α-methoxy-5-methyl-6,7-benzomorphan; or the hydrochloride, fumarate or tartrate salt thereof.

7. (—)-2-Cyclobutylmethyl-2'-hydroxy-9α-methoxy-5-methyl-6,7-benzomorphan; or the hydrochloride, fumarate or tartrate salt thereof.

8. (—)-2-Allyl-2'-hydroxy-9α-methoxy-5-methyl-6,7-benzomorphan; or the hydrochloride, fumarate or tartrate salt thereof.

9. (—)-2-Cyclopropylmethyl-9α-ethoxy-2'-hydroxy-5-methyl-6,7-benzomorphan; or the hydrochloride, tartrate or fumarate salt thereof.

10. (—)-2-Cyclopropylmethyl-2'-hydroxy-9α-methoxy-5-Allyl-6,7-Benzomorphan; or the hydrochloride, tartrate or fumarate salt thereof.

11. (—)-2-Cyclobutylmethyl-2'-hydroxy-9α-methoxy-5-Allyl-6,7-benzomorphan; or the hydrochloride, tartrate of fumarate salt thereof.

12. (—)-2-Cyclopropylmethyl-2'-hydroxy-9α-methoxy-5-propyl-6,7-benzomorphan; or the hydrochloride, fumarate or tartrate salt thereof.

13.     (−)-2-Cyclobutylmethyl-2′-hydroxy-9α-methoxy-5-propyl-6,7-benzomorphan; or the hydrochloride, fumarate or tartrate salt thereof.

14. A compound having the formula

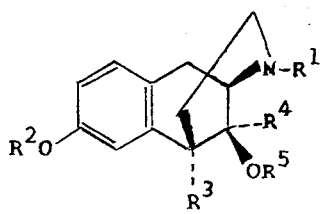

wherein R¹ is selected from the group consisting of H, —CH₂—C ≡ CH, —CH₂—CH=CH₂,

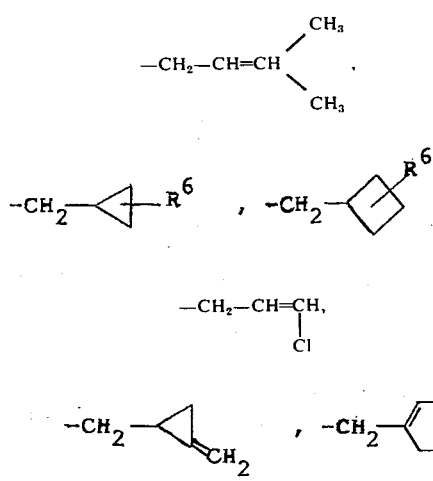

and

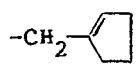

in which R⁶ is H or CH₃; R² is selected from the group consisting of H, (lower)alkyl, (lower)alkanoyl,

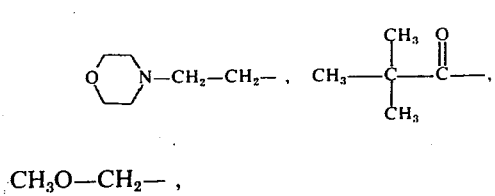

CH₃O—CH₂— ,

R⁵ is selected from the group consisting of (lower)alkyl, allyl and propargyl, R⁴ is H or (lower)alkyl and R³ is (lower)alkyl or (lower)alkenyl; or a pharmaceutically acceptable acid addition salt thereof.

15. A compound of claim 14 wherein R¹ is —CH₂—C ≡ CH, —CH₂—CH=CH₂,

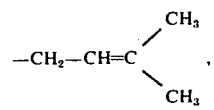

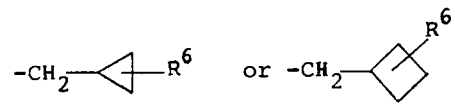

in which R⁶ is H or CH₃, R² is H, CH₃,

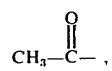

or

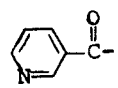

and R⁵ is CH₃, C₂H₅, propyl, allyl or propargyl, R⁴ is H and R³ is CH₃, ethyl, propyl or allyl; or a pharmaceutically acceptable acid addition salt thereof.

16. A compound of claim 14 wherein R¹ is —CH₂—CH=CH₂,

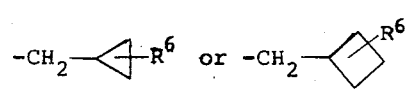

in which R⁶ is H or CH₃, R² is H, CH₃,

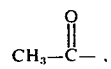

or

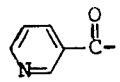

and R⁵ is CH₃, C₂H₅, propyl, allyl or propargyl, R⁴ is H and R³ is CH₃; or a pharmaceutically acceptable acid addition salt thereof.

17. A compound of claim 14 wherein R¹ is

or —CH₂—CH=CH₂,
R² is H, CH₃ or

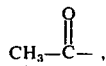

R⁵ is methyl, R⁴ is H and R³ is methyl; or a pharmaceutically acceptable acid addition salt thereof.

18. (−)-5-Allyl-2-cyclobutylmethyl-2'-hydroxy-9β-methoxy-6,7-benzomorphan; or the hydrochloride, tartrate or fumarate salt thereof.

19. (−)-5-Allyl-2-cyclobutylmethyl-2'-hydroxy-9β-methoxy-9α-methyl-6,7-benzomorphan; or the hydrochloride, fumarate or tartrate salt thereof.

20. (−)-5-Allyl-2-cyclobutylmethyl-2'-hydroxy-9α-methoxy-9β-methyl-6,7-benzomorphan; or the hydrochloride, tartrate or fumarate salt thereof.

21. (−)-2-Cyclobutylmethyl-2'-hydroxy-9α-methoxy-9β-methyl-5-n-propyl-6,7-benzomorphan; or the hydrochloride, tartrate or fumarate salt thereof.

22. (−)-5-Allyl-2-cyclopropylmethyl-2'-hydroxy-9α-methoxy-9β-methyl-6,7-benzomorphan; or the hydrochloride, tartrate or fumarate salt thereof.

23. (−)-2-Cyclopropyl-methyl-2'-hydroxy-9α-methoxy-9β-methyl-5-n-propyl-6,7-benzomorphan; or the hydrochloride, tartrate or fumarate salt thereof.

24. A compound having the formula

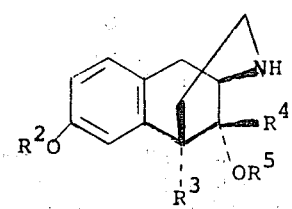

in which R² is (lower)alkyl, R³ is (lower)alkyl or (lower)alkenyl, R⁴ is H or (lower)alkyl and R⁵ is (lower)alkyl, allyl or propargyl; or an acid addition salt thereof.

25. A compound of claim 24 wherein R² is methyl, R³ is methyl, ethyl, n-propyl or allyl, R⁴ is H or methyl and R⁵ is methyl, ethyl or n-propyl; or an acid addition salt thereof.

26. The compound of claim 24 wherein R², R³ and R⁵ are methyl and R⁴ is H; or an acid addition salt thereof.

27. The essentially pure levorotatory isomers of the compounds of claim 24.

28. The essentially pure dextrorotatory isomers of the compound of claim 24.

29. The essentially pure levorotatory isomer of the compound of claim 26.

30. A compound of claim 24 wherein R² is methyl, R³ is allyl or n-propyl, R⁴ is H or methyl and R⁵ is methyl; or an acid addition salt thereof.

31. The essentially pure levorotatory isomer of the compound of claim 30.

32. A compound having the formula

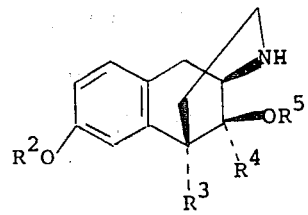

in which R² is (lower)alkyl, R³ is (lower)alkyl or (lower)alkenyl, R⁴ is H or (lower)alkyl and R⁵ is (lower)alkyl, allyl or propargyl; or an acid addition salt thereof.

33. (−)-2-Cyclopropylmethyl-2', 9α-dimethoxy-5-methyl-6,7-benzomorphan; or the hydrochloride, tartrate or fumarate salt thereof.

34. (±)-2-Cyclopropylmethyl-2', 9α-dimethoxy-5-methyl-6,7-benzomorphan; or the hydrochloride, tartrate or fumarate salt thereof.

* * * * *